(12) United States Patent
Eliu et al.

(10) Patent No.: US 7,811,335 B2
(45) Date of Patent: Oct. 12, 2010

(54) STYRYL SULFIDE DYES

(75) Inventors: Victor Paul Eliu, Lörrach (DE); Beate Fröhling, Grenzach-Wyhlen (DE); Dominique Kauffmann, Illzach (FR)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 0 days.

(21) Appl. No.: 11/922,069

(22) PCT Filed: Jun. 7, 2006

(86) PCT No.: PCT/EP2006/062946

§ 371 (c)(1),
(2), (4) Date: Sep. 9, 2009

(87) PCT Pub. No.: WO2006/134043

PCT Pub. Date: Dec. 21, 2006

(65) Prior Publication Data

US 2010/0000028 A1 Jan. 7, 2010

(30) Foreign Application Priority Data

Jun. 16, 2005 (EP) ................... 05105283

(51) Int. Cl.
*A61Q 5/10* (2006.01)
*C07C 321/00* (2006.01)
(52) U.S. Cl. ............. 8/405; 8/407; 8/432; 8/465; 8/568; 8/587; 8/650; 562/426; 132/202; 132/208
(58) Field of Classification Search .......... 8/405, 8/407, 432, 465, 568, 587, 650; 132/202, 132/208; 562/426
See application file for complete search history.

(56) References Cited

U.S. PATENT DOCUMENTS 3,225,025 A 12/1965 Jeremias et al. ............. 260/176
2007/0214580 A1 9/2007 Eliu et al. .................. 8/407

FOREIGN PATENT DOCUMENTS

| EP | 1647580 | 4/2006 |
| GB | 945542 | 1/1964 |
| WO | 95/01772 | 1/1995 |
| WO | 99/20234 | 4/1999 |
| WO | 03/099242 | 12/2003 |

OTHER PUBLICATIONS

STIC Search Report dated May 26, 2010.*
XP-002355460 (1998).*
English language abstract for EP 1647580, Apr. 19, 2006.
G. Ashwell et al., Journal of Materials Chemistry, vol. 15, (Jan. 2005), pp. 1160-1166.
K. Tsuboi et al., Mol. Cryst. Liq. Cryst., vol. 322, (1998), pp. 191-196.
K. Tsuboi et al., Jpn. J. Appl. Phys., vol. 42, Part 1, No. 2A, (Feb. 2003), pp. 607-613.
R. Naraoka et al., Chemical Physics Letters, vol. 362, Aug. 13, 2002, pp. 26-30.
K. Fujita et al., Langmuir, vol. 14, No. 26(Dec. 1998), pp. 7456-7462.
K. Kajikawa et al., Mol. Cryst. and Liq. Cryst., vol. 370, (2001), pp. 277-283.
H. Okawa et al., Molecular Crystals and Liquid Crystals, vol. 377, (2002), pp. 137-140.

* cited by examiner

*Primary Examiner*—Eisa B Elhilo
(74) *Attorney, Agent, or Firm*—Tyler A. Stevenson

(57) ABSTRACT

Disclosed are composition and method for dyeing keratin-containing fibers comprising or utilizing styryl sulfide dyes of formula (1), their salts, isomers, hydrates and other solvates, wherein $R_1$, $R'_1$, $R_2$, $R'_2$, $R_3$, $R'_3$, $W_1$, $W'_1$, $W_2$, $W'_2$, $W_3$, $W'_3$, $W_4$, $W'_4$, Q, Q', $Y_1$ and $Y_2$ are defined in claims and disclosure.

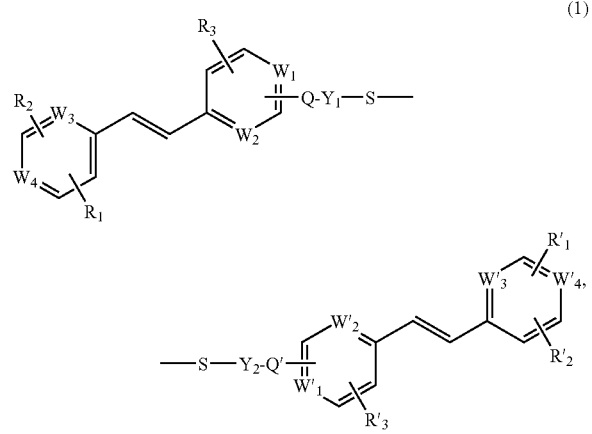

19 Claims, No Drawings

STYRYL SULFIDE DYES

The present invention relates to novel styryl sulfide dyes, compositions thereof, to processes for their preparation and to their use for the dyeing of organic materials, such as keratin fibers, wool, leather, silk, cellulose or polyamides, especially keratin-containing fibers, cotton or nylon, and preferably hair, more preferably human hair.

It is known, for example, from WO 95/01772 that cationic dyes can be used for the dyeing of organic material, for example keratin, silk, cellulose or cellulose derivatives, and also synthetic fibers, for example polyamides. Cationic dyes exhibit very brilliant shades. A disadvantage is their unsatisfactory fastness to washing.

R. S. Asquith, P. Carthew and T. T. Francis describe in JSDC from May 1973, pages 168-172 that ortho-azo disulfide dyes do not lead to covalent bonding with keratin fiber of wool, and that para-azo disulfide dyes underwent only at high concentration some covalent bindings with wool.

The technical problem is to provide dyes that are distinguished by deep dying having good fastness properties with respect to washing, light, shampooing and rubbing.

Accordingly, the present invention relates to a method of dyeing keratin-containing fibers, comprising treating the fiber with at least one styryl disulfide dye of formula

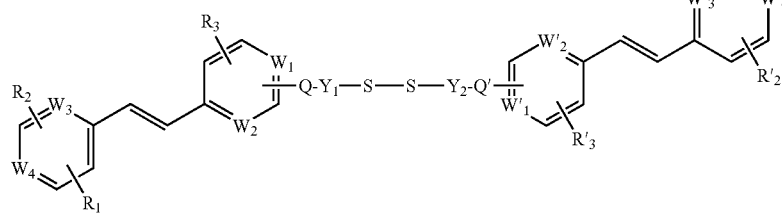

(1)

their salts, isomers, hydrates and other solvates, wherein $R_1$, $R'_1$, $R_2$, $R'_2$, $R_3$ and $R'_3$, independently from each other are hydrogen; $C_1$-$C_{20}$alkyl or $C_1$-$C_{20}$alkoxy, which may be substituted by one or more $C_1$-$C_5$alkoxy, halogen, —$NH_2$, mono-$C_1$-$C_5$alkylamino, di-$C_1$-$C_5$alkylamino, —$NO_2$ or hydroxy; $C_3$-$C_6$cycloalkyl; —C(O)H; —C(O)—$C_1$-$C_5$alkyl; halogen; $NO_2$; OH; phenyl, which may be substituted by one or more $C_1$-$C_5$alkyl, $C_1$-$C_5$alkoxy, halogen, —$NH_2$, mono-$C_1$-$C_5$alkylamino, di-$C_1$-$C_5$alkylamino, —$NO_2$ or hydroxy; or a radical of formula —$NR_4R_5$, wherein $R_4$ and $R_5$ independently from each other are hydrogen; $C_1$-$C_{12}$alkyl, which may be substituted by one or more $C_1$-$C_5$alkyl, $C_1$-$C_5$-alkoxy, hydroxy or —(CO)—H; —(CO)—$C_1$-$C_5$alkyl; phenyl or phenyl-$C_1$-$C_4$alkyl, wherein the phenyl moiety may be substituted by one or more $C_1$-$C_5$alkyl, $C_1$-$C_5$alkoxy, halogen, —$NH_2$, mono-$C_1$-$C_5$alkylamino, di-$C_1$-$C_5$alkylamino, —$NO_2$, carboxy or hydroxy;

$W_1$, $W'_1$, $W_2$, $W'_2$, $W_3$, $W'_3$, $W_4$ or $W'_4$, independently from each other are —CH— or —$N^+$—; wherein only one of $W_1$/$W'_1$, $W_2$/$W'_2$, $W_3$/$W'_3$, $W_4$/$W'_4$ is —$N^+$; and the bivalent radical -Q-Z—Y—S—S—Y'—Z'-Q'- is bonded to $W_1$ or $W_2$ and $W'_1$ or $W'_2$ respectively;

$Y_1$ and $Y_2$ independently from each other are $C_1$-$C_{10}$alkylene; $C_5$-$C_{10}$cycloalkylene; $C_5$-$C_{12}$arylene; or $C_5$-$C_{12}$arylene-($C_1$-$C_{10}$alkylene);

Q and Q' independently from each other are the direct bond; or —C(O)—; —C(O)O—; —OCO—; —N($R_6$)—;

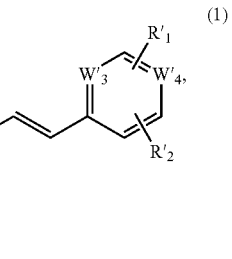

—C(O)N($R_6$); —($R_6$)NC(O)—; —O—; —S—; —S(O)—; or —S(O)$_2$—; and $R_6$ and $R_7$ independently from each other are hydrogen; $C_1$-$C_{14}$alkyl; $C_2$-$C_{14}$alkenyl; $C_6$-$C_{12}$aryl; $C_6$-$C_{12}$aryl-$C_1$-$C_{10}$alkyl; or $C_1$-$C_{10}$alkyl($C_5$-$C_{12}$aryl).

Preferably $Y_1$ and $Y_2$ are unsubstituted or substituted straight-chain or branched interrupted or uninterrupted $C_1$-$C_{10}$alkylene; or $C_5$-$C_{10}$cycloalkylene, and most preferably $C_1$-$C_5$alkylene.

Compounds of formula (1) are preferably used, wherein $R_1$, $R'_1$, $R_2$, $R'_2$, $R_3$ and $R'_3$, independently from each other are hydrogen; $C_1$-$C_6$alkyl; $NO_2$; or a radical of formula (1a) —$NR_4R_5$, wherein $R_4$ and $R_5$ independently from each other are hydrogen; or $C_1$-$C_5$alkyl.

Most preferably $R_1$, $R'_1$, $R_2$, $R'_2$, $R_3$ and $R'_3$, independently from each other are hydrogen; $C_1$-$C_5$alkyl; $NO_2$; or $NH_2$.

Mostly preferred in the present process are compounds of formula (1), wherein $R_1$, $R'_1$, $R_2$, $R'_2$, $R_3$ and $R'_3$ are hydrogen.

Preferably in the process of the present invention Q and Q' are the direct bond or —($R_6$)NC(O)—, wherein $R_6$ is hydrogen; or $C_1$-$C_5$alkyl.

Most preferred styryl sulfide dyes correspond to formula

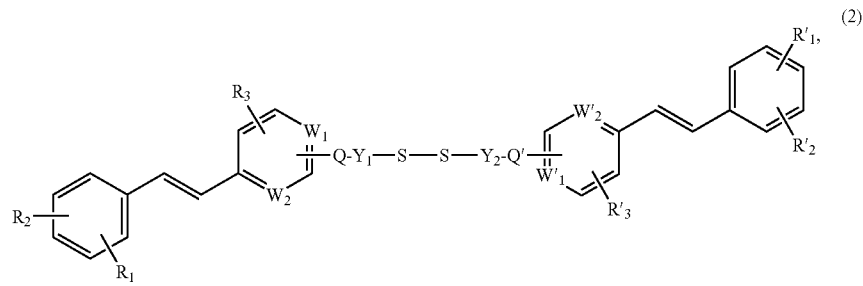

(2)

wherein one of the $W_1/W'_1$ or $W_2/W'_2$, is —$N^+$— the other is —CH—; and the biradical -Q-S—S—Y—Y'-Q'- is bonded to —$N^+$—; and $R_1$, $R'_1$, $R_2$, $R'_2$, $R_3$, $R'_3$, Q, Q', Y and Y' are defined as in formula (1).

Most preferred are styryl sulfide dyes of formula

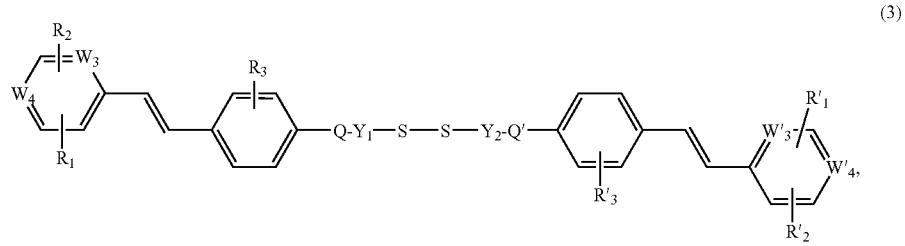
(3)

wherein one of the $W_3/W'_3$ or $W_4/W'_4$ is —$N^+$—, the other is —CH—; and $R_1$, $R'_1$, $R_2$, $R'_2$, $R_3$, $R'_3$, Q, Q', Y and Y' are defined as in formula (1).

Mostly preferred for the method of the present invention are the compounds of formula

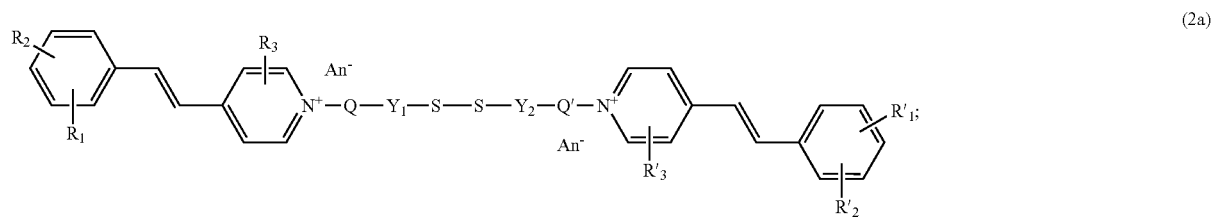
(2a)

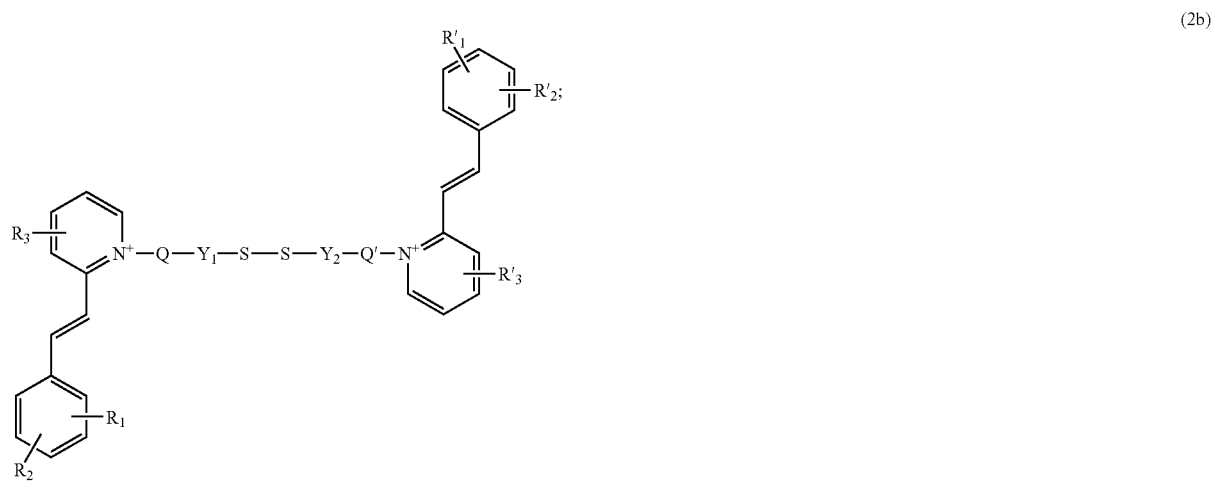
(2b)

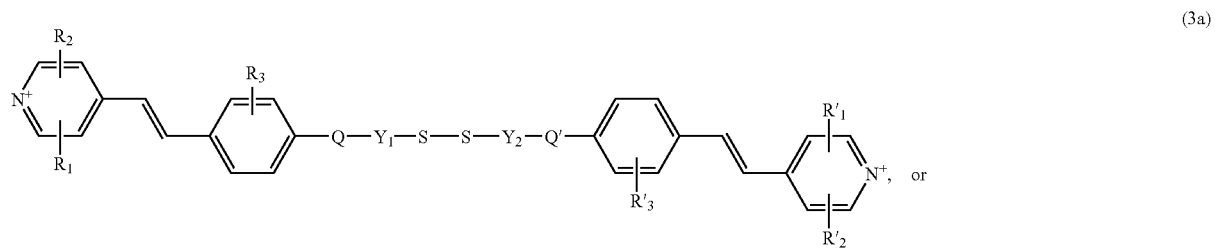
(3a)

-continued
(3b)
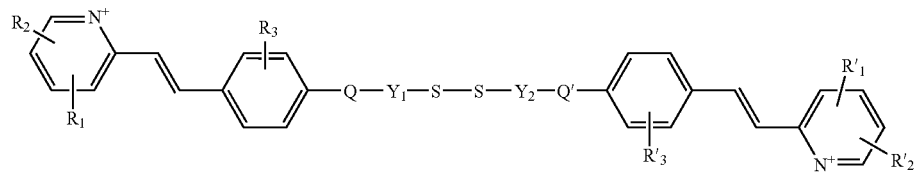
wherein
$R_1, R'_1, R_2, R'_2, R_3, R'_3, Q, Q', Y$ and $Y'$ are defined as formula (1).
In the styryl sulfide dyes used in the present invention preferably
$R_1$ is identical to $R_1'$;
$R_2$ is identical to $R_2'$;
$R_3$ is identical to $R_3'$;
Q is identical to Q'; and
$Y_1$ is identical to $Y_2$.
Exemplary compounds ust in the process of the present invention, are:
(101)
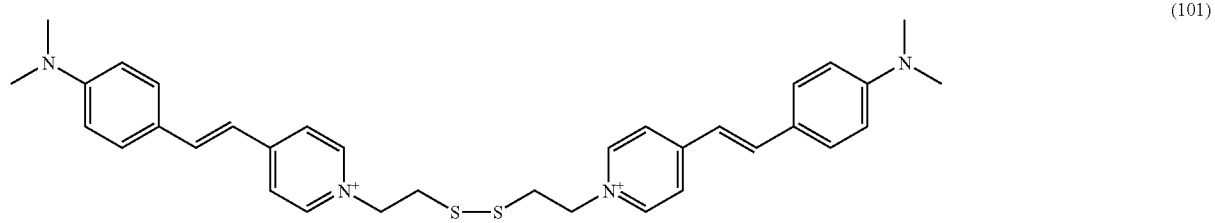
(102)
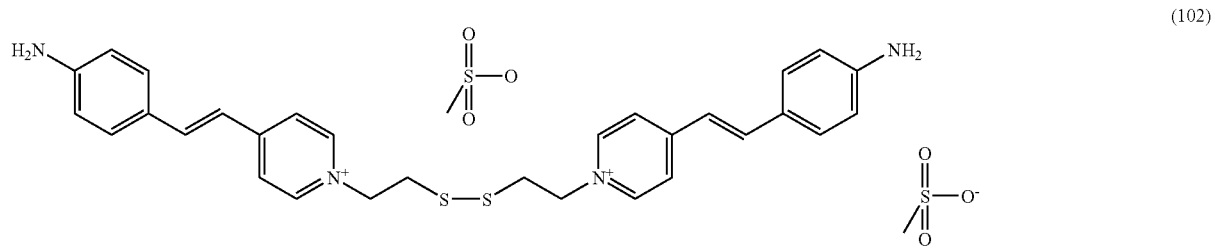
(103)
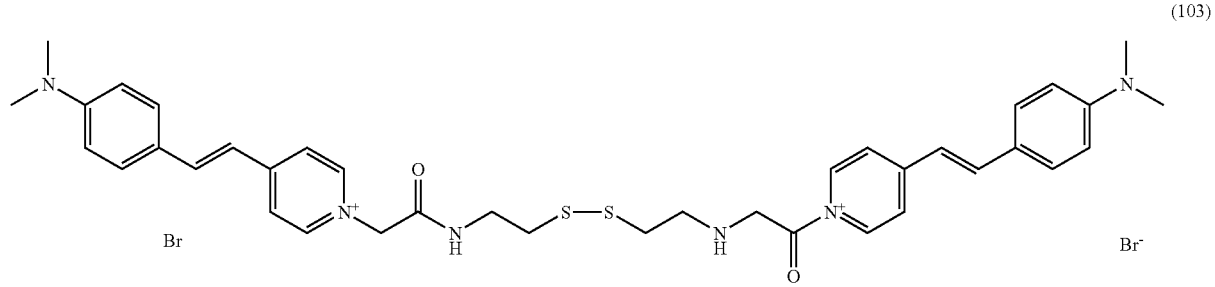
(104)
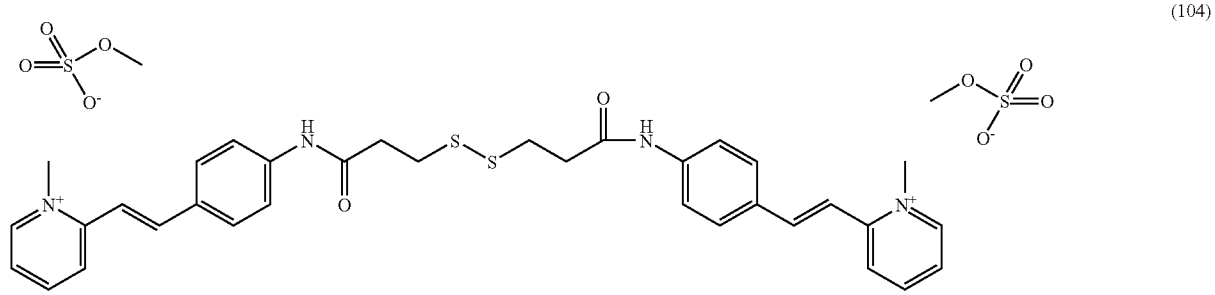

-continued
(105)
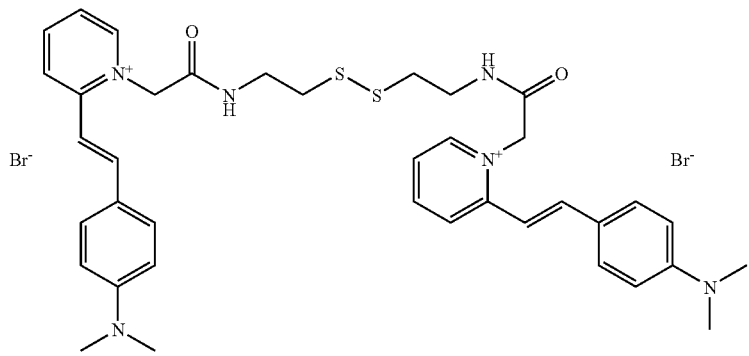
(106)
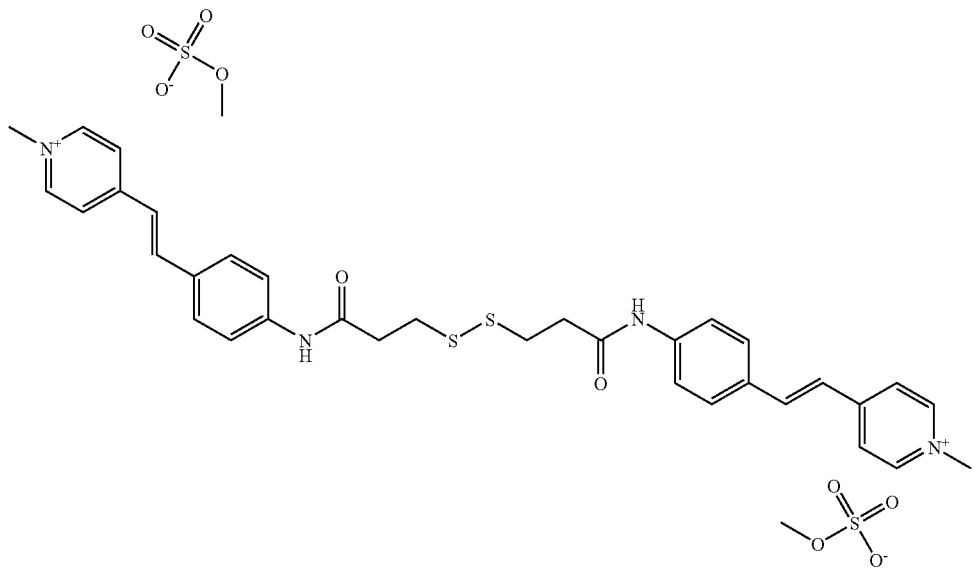
(107)
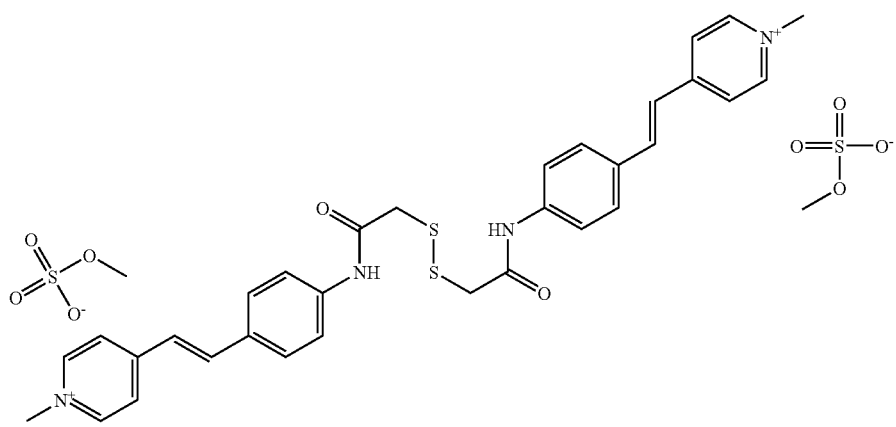
(108)
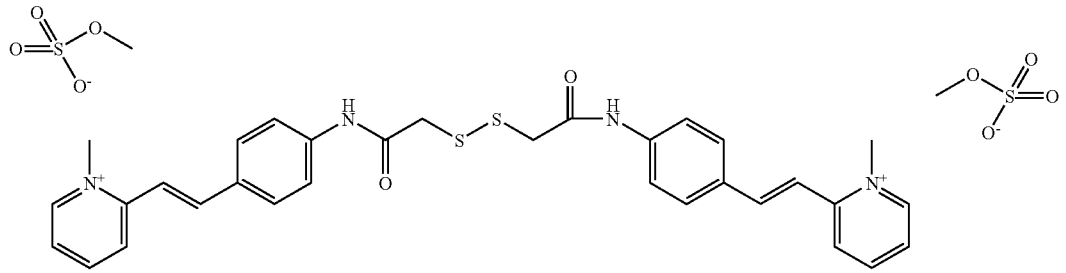

-continued

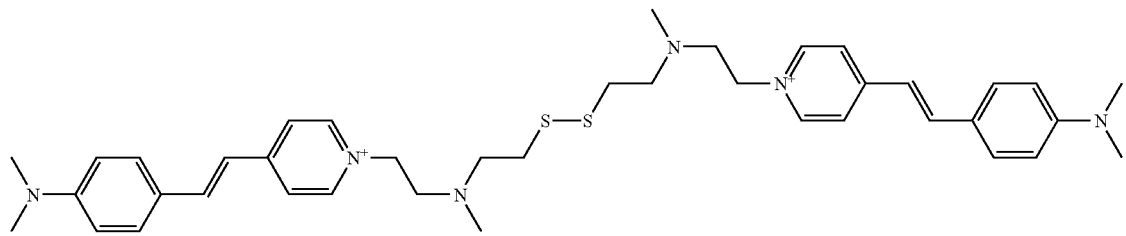

(109)

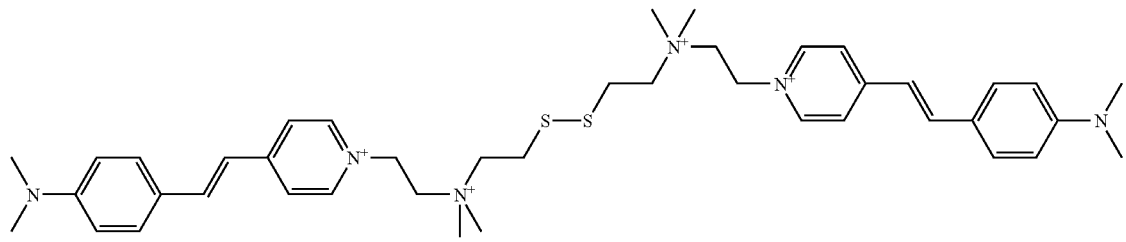

(110)

Alkylene is generally $C_1$-$C_{12}$alkylene, for example methylene, ethylene, propylene, isopropylene, n-butylene, sec-butylene, tert-butylene, n-pentylene, 2-pentylene 3-pentylene, 2,2'-dimethylpropylene, cyclopentylene, cyclohexylene, n-hexylene, n-octylene, 1,1',3,3'-tetramethylbutylene, 2-ethylhexylene, nonylene or decylene.

Alkylene may be straight-chain, branched, or, from $C_5$alkyl upwards, monocyclic or polycyclic, and may be interrupted by hetero atoms, such as such as O, S, —CO—, N, NH, $NR_{54}$, —OCO—, —CO($OR_4$)—, —$CONR_4$—, —($R_5$)NC(O)—; for example $C_1$-$C_{10}$alkylene may be a resisue such as: —$CH_2CH_2$—O—$CH_2CH_2$—O—$CH_2CH_2$—, or —$CH_2CH_2$—O—$CH_2CH_2$—, —$CH_2CH_2$—O—$CH_2$—, —$CH_2$—O—$CH_2$—, —$CH_2CH_2CH_2CH_2$—O—$CH_2CH_2$—, —$CH_2CH_2$—CH(N($CH_3$)$_2$)—$CH_2$—$CH_2$—, $CH_2$—$NH_2$—$CH_2$—$CH_2$, or —$CH_2CH_2$—NH—$CH_2CH_2$—, —$CH_2CH_2$—$NCH_3$—$CH_2CH_2$—, or —CO—$CH_2$—, or —$CH_2CO$—, or —$CH_2CH_2$—NHCO—$CH_2CH_2$—, or —$CH_2CH_2$—CONH—$CH_3$—$CH_2CH_2$—, —$CH_2CH_2$—$NCH_3$CO—$CH_2CH_2$—, or —$CH_2CH_2$—CON$CH_3$—$CH_3$—$CH_2CH_2$—, or —$CH_2$—NHCO—$CH_2CH_2$—, or —$CH_2CH_2$—NHCO—$CH_2$—, or —$CH_2CH_2$—CONH—$CH_2$— or —$CH_2$—CONH—$CH_2CH_2$—.

Arylene is generally $C_6$-$C_{12}$arylene; for example phenyl or naphthyl;

Arylalkylene is for example $C_5$-$C_{12}$aryl-$C_1$-$C_{10}$alkylene, $C_6$-$C_{12}$aryl-$C_1$-$C_2$alkylene, alkylarylene is for example $C_1$-$C_{10}$alkyl-$C_5$-$C_{12}$arylene or $C_1$-$C_2$alkyl-$C_6$-$C_{12}$arylene.

$C_5$-$C_{10}$cycloalkylene is for example cyclopentylene, cyclohexylene, morpholylene or piperidinylene.

$C_1$-$C_{16}$alkyl is for example, methyl, ethyl, propyl, isopropyl, n-butyl, sec-butyl, tert-butyl, n-pentyl, 2-pentyl, 3-pentyl, 2,2'-dimethylpropyl, cyclopentyl, cyclohexyl, n-hexyl, n-octyl, 1,1',3,3'-tetramethylbutyl or 2-ethylhexyl, nonyl, decyl, undecy, dodecyl, tredecyl, tetradecyl, pentadecyl or haxadecly.

$C_1$-$C_6$alkoxy is preferably methoxy, ethoxy, propoxy, butoxy, pentyloxy or hexyloxy.

$C_5$-$C_{12}$aryl-$C_1$-$C_{10}$alkylene is, for example, phenyl-$C_1$-$C_{10}$alkylene or naphthyl-$C_1$-$C_{10}$alkylene.

$C_6$-$C_{12}$aryl-$C_1$-$C_2$alkylene and $C_1$-$C_2$alkyl-$C_6$-$C_{12}$arylene are, for example, phenyl-$C_1$-$C_{10}$alkylene or naphthyl-$C_1$-$C_{10}$alkylene.

Halide is, for example, fluoride, chloride, bromide or iodide, especially chloride and fluoride.

"Anion" denotes, for example, an organic or inorganic anion, such as halide, preferably chloride and fluoride, sulfate, hydrogen sulfate, phosphate, boron tetrafluoride, carbonate, bicarbonate, oxalate or $C_1$-$C_8$alkyl sulfate, especially methyl sulfate or ethyl sulfate; anion also denotes lactate, formiate, acetate, propionate or a complex anion, such as the zinc chloride double salt.

The anion is especially a halide, preferably chloride or fluoride, sulfate, hydrogen sulfate, methyl sulfate, ethyl sulfate, phosphate, formiate, acetate or lactate.

The anion is more especially fluoride, chloride, methyl sulfate, ethyl sulfate, formate or acetate.

The compounds of formula

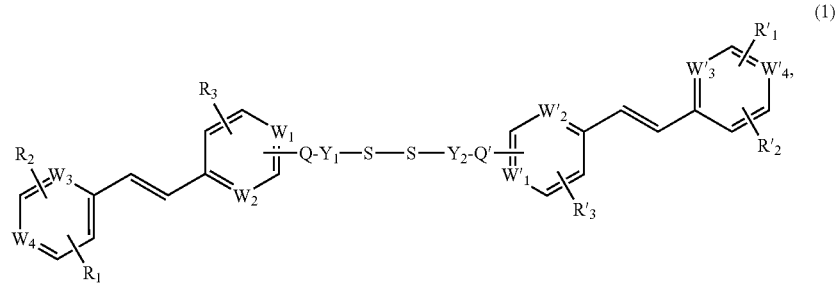

(1)

wherein $R_1$, $R'_1$, $R_2$, $R'_2$, $R_3$ and $R'_3$, independently from each other are hydrogen; $C_1$-$C_{20}$alkyl or $C_1$-$C_{20}$alkoxy, which may be substituted by one or more $C_1$-$C_5$alkoxy, halogen, —$NH_2$, mono-$C_1$-$C_5$alkylamino, di-$C_1$-$C_5$alkylamino, —$NO_2$ or hydroxy; $C_3$-$C_6$cycloalkyl; —C(O)H; —C(O)—$C_1$-$C_5$alkyl; halogen; $NO_2$; OH; phenyl, which may be substituted by one or more $C_1$-$C_5$alkyl, $C_1$-$C_5$alkoxy, halogen, —$NH_2$, mono-$C_1$-$C_5$alkylamino, di-$C_1$-$C_5$alkylamino, —$NO_2$ or hydroxy; or a radical of formula —$NR_4R_5$, wherein $R_4$ and $R_5$ independently from each other are hydrogen; $C_1$-$C_{12}$alkyl, which may be substituted by one or more $C_1$-$C_5$alkyl, $C_1$-$C_5$-alkoxy, hydroxy or —(CO)—H; —(CO)—$C_1$-$C_5$alkyl; phenyl or phenyl-$C_1$-$C_4$alkyl, wherein the phenyl moiety may be substituted by one or more $C_1$-$C_5$alkyl, $C_1$-$C_5$alkoxy, halogen, —$NH_2$, mono-$C_1$-$C_5$alkylamino, di-$C_1$-$C_5$alkylamino, —$NO_2$, carboxy or hydroxy;

$W_1$, $W'_1$, $W_2$, $W'_2$, $W_3$, $W'_3$, $W_4$ or $W'_4$, independently from each other are —CH— or —$N^+$—; wherein only one of $W_1/W'_1$, $W_2/W'_2$, $W_3/W'_3$, $W_4/W'_4$ is —$N^+$; and the bivalent radical -Q-Z—Y—S—S—Y'—Z'-Q'- is bonded to $W_1$ or $W_2$ and $W'_1$ or $W'_2$ respectively;

$Y_1$ and $Y_2$ independently from each other are $C_1$-$C_{10}$alkylene; $C_5$-$C_{10}$cycloalkylene; $C_5$-$C_{12}$arylene; or $C_5$-$C_{12}$arylene-($C_1$-$C_{10}$alkylene);

Q and Q' independently from each other are the direct bond; or —C(O)—; —C(O)O—; —OCO—; —N($R_6$)—;

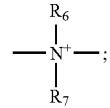

—C(O)N($R_6$)—; —($R_6$)NC(O)—; —O—; —S—; —S(O)—; or —S(O)$_2$—; and $R_6$ and $R_7$ independently from each other are hydrogen; $C_1$-$C_{14}$alkyl; $C_2$-$C_{14}$alkenyl; $C_6$-$C_{12}$aryl; $C_6$-$C_{12}$aryl-$C_1$-$C_{10}$-alkyl; or $C_1$-$C_{10}$alkyl($C_5$-$C_{12}$aryl);

are novel and represent a further embodiment of the present invention

A further embodiment of the present invention relates to processes for the preparation of the dyes of formula (1).

The compounds are prepared according to the following reaction scheme:

Step 1:

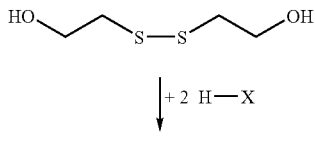

Step 2:

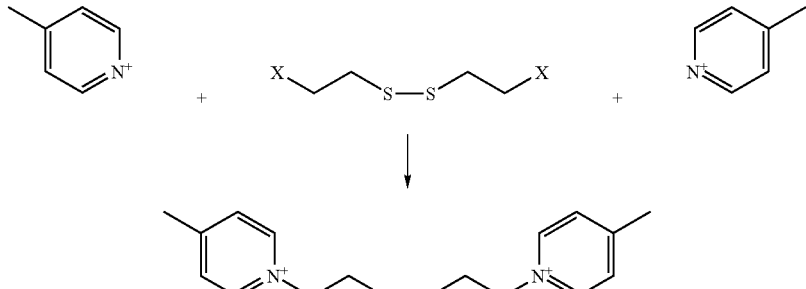

Step 3:

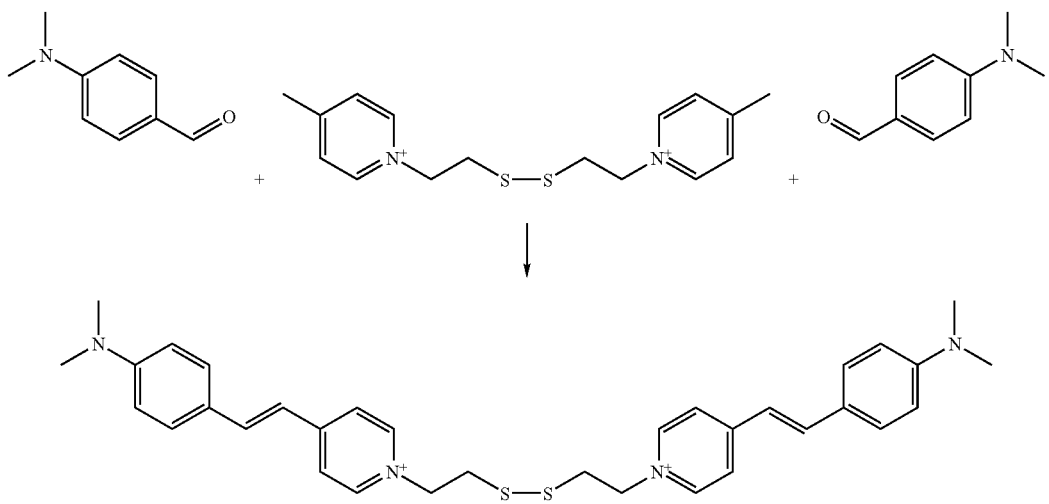

The 3rd reaction step may be carried out in solvents like water, alcohols, like methanol, ethanol, 2-propanol or butanol; nitriles, like acetonitrile or propionitrile; amides, like dimethylformamides, dimethylacetamide, N-methylpyrolidone; chlorinated hydrocarbons like chloroform, chlorbrenzene or trichloroethylene; or other solvents like dimethylsulfoxide.

Customary, the temperature is in the range of 273 to 393 K, preferably 300 to 370 K during the mixing of the starting compounds.

The reaction time is generally dependent on the reactivity of the starting compounds, on the selected reaction temperature and on the desired conversion. The selected reaction time is usually in the range from one hour to three days.

The selected reaction pressure is generally in the range from 0.1 to 10 bar especially from 0.2 to 3.0 bar and is more especially atmospheric pressure.

It may by desirable to conduct the reaction of compounds in the presence of a catalyst.

Suitable catalysts are for example an alkali metal $C_1$-$C_6$alkyloxide, such as sodium-, potassium or lithium $C_1$-$C_6$alkyloxide, preferably sodium methoxide, potassium methoxide or lithium methoxide, or sodium ethoxide, potassium ethoxide or lithium ethoxide; or secondary ortertiary amines, for example, such as chinuclidine, piperidine, N-methylpiperidine, pyridine, trimethylamine, dimethylamine, diethylamine, triethylamine, trioctylamine, 1,4-diazabicyclo-[2.2.2]octan, chinuclidine, N-methylpiperidine; or alkalimetal acetate, for example such as sodium acetate, potassium acetate, or lithium acetate.

Preferred are potassium acetate, sodium methoxide, pyridine and 1,4-diazabicyclo[2.2.2]-octan, piperidine.

The molar ratio of compound of formula (1a) to the catalyst is generally selected in the range from 10:1 to 1:5, especially in the range from 10:1 to 1:1.

The product prepared according to the process of the present invention may be advantageously worked up and isolated, and if desired be purified.

Customary, the work up starts by decreasing the temperature of the reaction mixture in the range from 280 to 350 K, especially in the range from 290 to 320 K.

It may be advantageous to decrease the temperature slowly, over a period of several hours.

In general, the reaction product is usually filtered off and then washed with water, a solvent or a salt solution and subsequently dried.

Filtration is normally carried out in standard filtering equipment, for example Büchner funnels, filter presses, pressurised suction filters, preferably in vacuo.

The temperature for the drying is dependent on the applied pressure. Drying is usually carried out in vacuo at 50-200 mbar.

The drying is usually carried out at a temperature in the range from 313 to 363 K, especially from 323 to 353 K, and more especially in the range from 328 to 348 K.

Advantageously the product is purified by recrystallisation after isolation.

Organic solvents and solvent mixtures are suitable for the recrystallisation, preferably alcohols, for example methanol, ethanol, 2-propanol or butanol, especially 2-propanol.

The dyes of formula (1) according to the invention are suitable for dyeing organic materials, such as keratin-containing fibers, wool, leather, silk, cellulose or polyamides, cotton or nylon, and preferably human hair. The dyeings obtained are distinguished by their depth of shade and their good fastness properties to washing, such as, for example, fastness to light, shampooing and rubbing. The stability, in particular the storage stability of the dyes according to the invention are excellent.

Generally, hair dyeing agents on a synthetic base may be classified into three groups:
temporary dyeing agents
semipermanent dyeing agents, and
permanent dyeing agents.

The multiplicity of shades of the dyes can be increased by combination with other dyes.

Therefore the dyes of formula (1) of the present invention may be combined with dyes of the same or other classes of dyes, especially with direct dyes, oxidation dyes; dye precursor combinations of a coupler compound as well as a diazotized compound, or a capped diazotized compound and/or cationic reactive dyes.

Direct dyes are of natural origin or may be prepared synthetically. They are uncharged, cationic or anionic, such as acid dyes.

The dyes of formula (1) may be used in combination with at least one single direct dye different from the dyes of formula (1).

Direct dyes do not require any addition of an oxidizing agent to develop their dyeing effect. Accordingly the dyeing results are less permanent than those obtained with permanent dyeing compositions. Direct dyes are therefore preferably used for semipermanent hair dyeings.

Examples of direct dyes are described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, and in "Europäisches Inventar der Kosmetikrohstoffe", 1996, published by The European Commission, obtainable in diskette form from the Bundesverband der deutschen Industrie—und Handelsunternehmen für Arzneimittel, Reformwaren und Körperpflegemittel e.V., Mannheim.

More preferred direct dyes which are useful for the combination with at least one single dye of formula (1), especially for semi permanent dyeing, are: 2-amino-3-nitrophenol, 2-amino-4-hydroxyethylamino-anisole sulfate, 2-amino-6-chloro-4-nitrophenol, 2-chloro-5-nitro-N-hydroxyethylene-p-phenylendiamine, 2-hydroxyethyl-picramic acid, 2,6-diamino-3-((pyridine-3yl)-azo)pyridine, 2-nitro-5-glyceryl-methylaniline, 3-methylamino-4-nitro-phenoxyethanol, 4-amino-2-nitrodiphenyleneamine-2'-carboxilic acid, 6-nitro-1,2,3,4,-tetrahydroquinoxaline, 4-N-ethyl-1,4-bis(2'-hydroxyethylamino-2-nitrobenzene hydrochloride, 1-methyl-3-nitro-4-(2'-hydroxyethyl)-aminobenzene, 3-nitro-p-hydroxyethyl-aminophenol, 4-amino-3-nitrophenol, 4-hydroxypropylamine-3-nitrophenol, hydroxyanthrylaminopropylmethyl morphlino methosulfate, 4-nitrophenyl-aminoethylurea, 6-nitro-p-toluidine, Acid Blue 62, Acid Blue 9, Acid Red 35, Acid Red 87 (Eosin), Acid Violet 43, Acid Yellow 1, Basic Blue 3, Basic Blue 6, Basic Blue 7, Basic Blue 9, Basic Blue 12, Basic Blue 26, Basic Blue 99, Basic Brown 16, Basic Brown 17, Basic Red 2, Basic Red 22, Basic Red 76, Basic Violet 14, Basic Yellow 57, Basic Yellow 9, Disperse Blue 3, Disperse Orange 3, Disperse Red 17, Disperse Violet 1, Disperse Violet 4, Disperse Black 9, Fast Green FCF, HC Blue 2, HC Blue 7, HC Blue 8, HC Blue 12, HC Orange 1, HC Orange 2, HC Red 1, HC Red 10-11, HC Red 13, HC Red 16, HC Red 3, HC Red BN, HC Red 7, HC Violet 1, HC Violet 2, HC Yellow 2, HC Yellow 5, HC Yellow 5, HC Yellow 6, HC Yellow 7, HC Yellow 9, HC Yellow 12, HC Red 8, hydroxyethyl-2-nitro-p-toluidine, N,N-Bis-(2-Hydroxyethyl)-2-nitro-p-phenylendiamine, HC Violet BS, Picramic Acid, Solvent Green 7.

Furthermore, the dyes of formula (1) may be combined with at least one cationic azo dye, for example the compounds disclosed in GB-A-2 319 776 as well as the oxazine dyes described in DE-A-299 12 327 and mixtures thereof with the other direct dyes mentioned therein, and even more preferred with cationic dyes such as Basic Yellow 87, Basic Orange 31 or Basic Red 51, or with cationic dyes as described in WO 01/66646, especially example 4, or with cationic dyes as described in WO 02/31056, especially example 6 (compound of formula 106); or the cationic dye of formula (3) as described in EP-A-714,954, or with a yellow cationic dye of formula

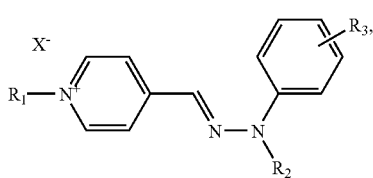

(DD1)

wherein $R_1$ and $R_2$ are each independently of the other a $C_1$-$C_8$alkyl; or an unsubstituted or substituted benzyl;

$R_3$ is hydrogen; $C_1$-$C_8$alkyl; $C_1$-$C_8$alkoxy; cyanide; or halide; preferably hydrogen; and $X^-$ is an anion; and preferably a compound of formula (DD1), wherein $R_1$ is methyl; $R_2$ is benzyl; $R_3$ is hydrogen; and $X^-$ is an anion; or wherein $R_1$ is benzyl; $R_2$ is benzyl; $R_3$ is hydrogen; and $X^-$ is an anion; or wherein $R_1$ is benzyl; $R_2$ is methyl; $R_3$ is hydrogen; and $X^-$ is an anion.

Furthermore, cationic nitroaniline and anthraquinone dyes are useful for a combination with a dye of formula (1), for example the dyes as described in the following patent specifications: U.S. Pat. No. 5,298,029, especially in col 2, l. 33 to col 5, l. 38; U.S. Pat. No. 5,360,930, especially in col 2, l. 38 to col 5, l. 49; U.S. Pat. No. 5,169,403, especially in col 2, l. 30 to col 5, l. 38; U.S. Pat. No. 5,256,823, especially in col 4, l. 23 to col 5, l. 15; U.S. Pat. No. 5,135,543, especially in col 4, l. 24 to col 5, l. 16; EP-A-818 193, especially on p. 2, l. 40 to p. 3, l. 26; U.S. Pat. No. 5,486,629, especially in col 2, l. 34 to col 5, l. 29; and EP-A-758 547, especially on p. 7, l. 48 to p. 8, l. 19.

The dyes of formula (1) may also be combined with acid dyes, for example the dyes which are known from the international names (Color index), or trade names.

Preferred acid dyes which are useful for the combination with a dye of formula (1) are described in U.S. Pat. No. 6,248,314. They include Red Color No. 120, Yellow Color No. 4, Yellow Color No. 5, Red Color No. 201, Red Color No. 227, Orange Color No. 205, Brown Color No. 201, Red Color No. 502, Red Color No. 503, Red Color No. 504, Red Color No. 506, Orange Color No. 402, Yellow Color No. 402, Yellow Color No. 406, Yellow Color No. 407, Red Color No. 213, Red Color No. 214, Red Color No. 3, Red Color No. 104, Red Color No. 105(1), Red Color No. 106, Green Color No. 2, Green Color No. 3, Orange Color No. 207, Yellow Color No. 202(1), Yellow Color No. 202(2), Yellow Color No. 202, Blue Color No. 203, Blue Color No. 205, Blue Color No. 2, Yellow Color No. 203, Blue Color No. 201, Green Color No. 201, Blue Color NO. 1, Red Color No. 230(1), Red Color No. 231, Red Color No. 232, Green Color No. 204, Green Color No. 205, Red Color No. 401, Yellow Color No. 403(1), Green Color No. 401, Green Color No. 402, Black Color No. 401 and Purple Color No. 401, especially Black Color No. 401, Purple Color 401, Orange Color No. 205.

These acid dyes may be used either as single component or in any combination thereof.

Hair dye compositions comprising an acid dye are known. They are for example described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, especially on p. 253 and 254.

Hair dye compositions which comprise an acid dye have a pH of 2-6, preferably 2-5, more preferably 2.5-4.0.

The dyes of formula (1) according to the present invention may also readily be used in combination with acid dyes and/or adjuvants, for example acid dyes and an alkylene carbonate, as described in U.S. Pat. No. 6,248,314, especially in examples 1 and 2;

acid hair dye compositions comprising various kinds of organic solvents represented by benzyl alcohol as a penetrant solvent have good penetrability into hair, as described in Japanese Patent Application Laid-Open Nos. 210023/1986 and 101841/1995;

acid hair dye compositions with a water-soluble polymer or the like to prevent the drooping of the hair dye composition, as described for example in Japanese Patent Application Laid-Open Nos. 87450/1998, 255540/1997 and 245348/1996;

acid hair dye compositions with a water-soluble polymer of aromatic alcohols, lower alkylene carbonates, or the like as described in Japanese Patent Application Laid-Open No. 53970/1998 and Japanese Patent Invention No. 23911/1973.

The dyes of formula (1) may also be combined with uncharged dyes, for example selected from the group of the nitroanilines, nitrophenylenediamines, nitroaminophenols, anthraquinones, indophenols, phenazines, phenothiazines, bispyrazolons, bispyrazol aza derivatives and methines.

Furthermore, the dyes of formula (1) may also be used in combination with oxidation dye systems.

Oxidation dyes, which, in the initial state, are not dyes but dye precursors are classified according to their chemical properties into developer and coupler compounds.

Suitable oxidation dyes are described for example in

DE 19 959 479, especially in col 2, l. 6 to col 3, l. 11;

"Dermatology", edited by Ch. Culnan, H. Maibach, Verlag Marcel Dekker Inc., New York, Basle, 1986, Vol. 7, Ch. Zviak, The Science of Hair Care, chapter 8, on p. 264-267 (oxidation dyes);

Preferred developer compounds are for example primary aromatic amines, which are substituted in the para- or ortho-position with a substituted or unsubstituted hydroxy- or amino residue, or diaminopyridine derivatives, heterocylic hydrazones, 4-aminopyrazol derivatives, 2,4,5,6-tetraminopyrimidine derivatives, or unsaturated aldehydes as described in DE 19 717 224, especially on p. 2, l. 50 to l. 66 and on p. 3 l. 8 to l. 12, or cationic developer compounds as described in WO 00/43367, especially on p. 21. 27 to p. 8, l. 24, in particular on p. 9, l. 22 to p. 11, l. 6.

Furthermore, developer compounds in their physiological compatible acid addition salt form, such as hydrochloride or sulfate can be used. Developer compounds, which have aromatic OH radicals are also suitable in their salt form together with a base, such as alkali metal-phenolates.

Preferred developer compounds are disclosed in DE 19959479, p. 2, l. 8-29.

More preferred developer compounds are p-phenylendiamine, p-toluoylendiamine, p-, m- o-aminophenol, N,N-bis-(2-hydroxyethyl)p-phenylenediamine sulfate, 2-amino-4-hydroxyethylaminoanisole sulfate, hydroxyethyl-3,4-methylenedioxyaniline, 1-(2'-hydroxyethyl-2,5-diaminobenzene, 2,6-dimethoxy-3,5-diamino-pyridine, hydroxypropyl-bis-(N-hydroxyethyl-p-phenylenediamine) hydrochloride, hydroxyethyl-p-phenylenediamine sulfate, 4-amino-3-methylphenol, 4-methylaminophenol sulfate, 2-aminomethyl-4-aminophenol, 4,5-diamino-1-(2-hydroxyethyl)-1H-pyrazol, 4-amino-m-cresol, 6-amino-m-cresol, 5-amino-6-chloro-cresol, 2,4,5,6-tetraminopyrimidine, 2-hydroxy-4,5,6-triaminopyrimidine or 4-hydroxy-2,5,6-triaminopyrimidine sulfate.

Preferred coupler compounds are m-phenylendiamine derivatives, naphthole, resorcine and resorcine derivatives, pyrazolone and m-aminophenol derivatives, and most preferably the coupler compounds disclosed in DE 19959479, p. 1, l. 33 to p. 3, l. 11.

The dyes of formula (1) may also be used together with unsaturated aldehydes as disclosed in DE 19 717 224 (p. 2, l. 50 to l. 66 and on p. 3 l. 8 to l. 12) which may be used as direct dyes or, alternatively together with oxidation dye precursors.

Further preferred for a combination with a dye of formula (1) are the following oxidation dye precursors:
the developer/-coupler combination 2,4,5,6-tetraminopyrimidine and 2-methylresorcine for assessing of red shades;
p-toluenediamine and 4-amino-2-hydroxytoluene for assessing of blue-violet shades;
p-toluenediamine and 2-amino-4-hydroxyethylaminoanisole for assessing of blue shades;
p-toluenediamine and 2,4-diamino-phenoxyethynol for assessing of blue shades;
methyl-4-aminophenol and 4-amino-2-hydroxytleoluene for assessing of orange shades;
p-toluenediamine and resorcine for assessing of brown-green shades;
p-toluenediamine and 1-naphthol for assessing of blue-violet shades, or
p-toluenediamine and 2-methylresorcine for assessing of brown-gold shades.

Furthermore, autooxidizable compounds may be used in combination with the dyes of formula (1).

Autooxidizable compounds are aromatic compounds with more than two substituents in the aomatic ring, which have a very low redox potential and will therefore be oxidized when exposed to the air. The dyeings obtained with these compounds are very stable and resistant to shampoo.

Autooxidizable compounds are for example benzene, indol, or indoline, especially 5,6-dihydroxyindol or 5,6-dihydroxyindoline derivatives as described in WO 99/20234, especially on p. 26, l. 10 to p. 28, l. 15, or in WO 00/28957 on p. 2, third paragraph.

Preferred autooxidizable benzene derivatives are 1,2,4-trihydroxybenzene, 1-methyl-2,4,5-trihydroxybenzene, 2,4-diamnio-6-methylphenol, 2-amino-4-methylaminophenol, 2,5-diamino-4-methyl-phenol, 2,6-diamino-4-diethylaminophenol, 2,6-diamino-1,4-dihydroxybenzene, and the salts of these compounds, which are accessible with acid.

Preferred autooxidizable indol derivatives are 5,6-dihydroxyindol, 2-methyl-5,6-dihydroxyindol, 3-methyl-5,6-dihydroxyindole, 1-methyl-5,6-dihydroxyindol, 2,3-dimethyl-5,6-dihydroxyindol, 5-methoxy-6-dihydroxyindol, 5-acetoxy-6-hydroxyindol, 5,6-diacetoxyindol, acid of 5,6-dihydroxyindol-2-carbonacid, and the salts of these compounds, which are accessible with acid.

The dyes of formula (1) may also be used in combination with naturally occurring dyes, such as henna red, henna neutral, henna black, camomile blossom, sandalwood, black tea, Rhamnus frangula bark, sage, campeche wood, madder root, catechu, sedre and alkanet root. Such dyeings are described, for example, in EP-A-404 868, especially on p. 3, l. 55 to p. 4, l. 9.

Furthermore, the dyes of formula (1) may also be used in combination with capped diazotised compounds.

Suitable diazotised compounds are for example the compounds of formulae (1)-(4) in WO 2004/019897 (bridging gages 1 and 2) and the corresponding watersoluble coupling components (I)-(IV) as disclosed in the same reference.

Further preferred dyes or dye combinations which are useful for the combination with a dye of formula (1) according to the present invention are described in (DC-01): WO 95/01772, wherein mixtures of at least two cationic dyes are disclosed, especially p. 2, l. 7 to p. 4, l. 1, preferably p. 4, l. 35 to p. 8, l. 21; formulations p. 11, last §-p. 28, l. 19;

(DC-02): U.S. Pat. No. 6,843,256, wherein cationic dyes are disclosed, especially the compounds of formulae (1), (2), (3) and (4) (col. 1, l. 27-col. 3, l. 20, and preferably the compounds as prepared in the examples 1 to 4 (col. 10, l. 42 to col. 13, l. 37; formulations col. 13, l. 38 to col. 15, l. 8;

(DC-03): EP 970 685, wherein direct dyes are described, especially p. 2, l. 44 to p. 9, l. 56 and preferably p. 9, l. 58 to p. 48, l. 12; processes for dyeing of keratin-containing fibers especially p. 50, l. 15 to 43; formulations p. 50, l. 46 to p. 51, l. 40;

(DC-04): DE-A-19 713 698, wherein direct dyes are described, especially p. 2, l. 61 to p. 3, l. 43; formulations p. 5, l. 26 to 60;

(DC-05): U.S. Pat. No. 6,368,360, wherein directd dyes (col. 4, l. 1 to col. 6, l. 31) and oxidizing agents (col. 6, l. 37-39) are disclosed; formulations col. 7, l. 47 to col. 9, l. 4;

(DC-06): EP 1 166 752, wherein cationic dyes (p. 3, l. 22-p. 4, l. 15) and anionic UV-absorbers (p. 4, l. 27-30) are disclosed; formulations p. 7, l. 50-p. 9, l. 56;

(DC-07): EP 998,908, wherein oxidation dyeings comprising a cationic direct dye and pyrazolo-[1,5-a]-pyrimidines (p. 2, l. 48-p. 4, l. 1) are disclosed; dyeing formulations p. 47, l. 25 to p. 50, l. 29;

(DC-08): FR-2788432, wherein combinations of cationic dyes with Arianors are disclosed, especially p. 53, l. 1 to p. 63, l. 23, more especially p. 51 to 52, most especially Basic Brown 17, Basic brown 16, Basic Red 76 and Basic Red 118, and/or at least one Basic Yellow 57, and/or at least one Basic Blue 99; or combinations of arianoren and/or oxidative dyes, especially p. 2, l. 16 to p. 3, l. 16; dyeing formulations on p. 53, l. 1 to p. 63, l. 23;

(DC-09): DE-A-19 713 698, wherein the combinations of direct dyes and permanent-wave fixing comprising an oxidation agent, an oxidation dye and a direct dye are disclosed; especially p. 4, l. 65 to p. 5, l. 59;

(DC-10): EP 850 638, wherein developer compounds and oxidizing agents are disclosed; especially p. 2, l. 27 to p. 7, l. 46 and preferably p. 7, l. 20 to p. 9, l. 26; dyeing formulations p. 2, l. 3-12 and l. 30 to p. 14, and p. 28, l. 35-p. 30, l. 20; preferably p. 30, l. 25-p. 32, l. 30;

(DC-11): U.S. Pat. No. 6,190,421 wherein extemporaneous mixtures of a composition (A) containing one or more oxidation dye precursors and optionally one or more couplers, of a composition (B), in powder form, containing one or more direct dyes (col. 5, l. 40-col. 7, l. 14), optionally dispersed in an organic pulverulent excipient and/or a mineral pulverulent excipient, and a composition (C) containing one or more oxidizing agents are disclosed; formulations col. 8, l. 60-col. 9, l. 56;

(DC-12): U.S. Pat. No. 6,228,129, wherein a ready-to-use composition comprising at least one oxidation base, at least one cationic direct dye and at least one enzyme of the 2-electron oxidoreductase type in the presence of at least one donor for the said enzyme are disclosed; especially col. 8, l. 17-col. 13, l. 65; dyeing formulations in col. 2, l. 16 to col. 25, l. 55, a multi-compartment dyeing device is described in col. 26, l. 13-24;

(DC-13): WO 99/20235, wherein compositions of at least one cationic dye and at least one nitrated benzene dye with cationic direct dyes and nitro benzene direct dyes are described; on p. 2, l. 1 to p. 7, l. 9, and p. 39, l. 1 to p. 40 l. 11, preferably p. 8, l. 12 to p. 25 l. 6, p. 26, l. 7 to p. 30, l. 15; p. 1, l. 25 to p. 8, l. 5, p. 30, l. 17 to p. 34 l. 25, p. 8, l. 12 to p. 25 l. 6, p. 35, l. 21 to 27, especially on p. 36, l. 1 to p. 37;

(DC-14): WO 99/20234, wherein compositions comprising at least one direct cationic dye and at least one autooxidisable dye, especially benzene, indol and indoline derivatives are described, preferably direct dyes on p. 2, l. 19 to p. 26, l. 4, and autooxidisable dyes as disclosed especially on p. 26, l. 10 to p. 28, l. 15; dyeing formulations especially on p. 34, l. 5 to p. 35, li 18;

(DC-15): EP 850 636, wherein oxidation dyeing compositions comprising at least one direct dye and at least one meta-aminophenol derivative as coupler component and at least one developer compound and an oxidizing agent are disclosed, especially p. 5, l. 41 to p. 7, l. 52, dyeing formulations p. 19, l. 50-p. 22, l. 12;

(DC-16): EP-A-850 637, wherein oxidation dyeing compositions comprising at least one oxidation base selected from para-phenylenediamines and bis(phenyl)alkylenediamines, and the acid-addition salts thereof, at least one coupler selected from meta-diphenols, and the acid-addition salts thereof, at least one cationic direct dye, and at least one oxidizing agent are disclosed, especially p. 6, l. 50 to p. 8, l. 44 are discloseded; dyeing formulations p. 21, l. 30-p. 22, l. 57;

(DC-17): WO 99/48856, wherein oxidation dyeing compositions comprising cationic couplers are disclosed, especially p. 9, l. 16-p. 13, l. 8, and p. 11, l. 20-p. 12, l. 13; dyeing formulations p. 36, l. 7-p. 39, l. 24;

(DC-18): DE 197 172 24, wherein dyeing agents comprising unsaturated aldehydes and coupler compounds and primary and secondary amino group compounds, nitrogen-containing heterocylic compounds, amino acids, oligopeptids, aromatic hydroxy compounds, and/or at least one CH-active compound are disclosed p. 3, l. 42-p. 5 l. 25; dyeing formulations p. 8, l. 25-p. 9, l. 61.

In the dye combinations disclosed in the references (DC-01-DC-18) above, the dyes of formula (1) according to the present invention may be added to the dye combinations or dyeing formulations or may be replaced with at least one dye of formula (1).

The present invention also relates to formulations, which are used for the dyeing of organic materials, preferably keratin-containing fibers, and most preferably human hair, comprising at least
(a) 0.001 to 5, preferably 0.005 to 4, more particularly 0.2 to 3% b.w. of at least one dye of formula (1);
(b) 1 to 40, preferably 5 to 30% b.w. of a solvent; and
(c) 0.01 to 20% b.w. of an adjuvant.

The formulations may be applied on the keratin-containing fiber, preferably the human hair in different technical forms.

Technical forms of formulations are for example a solution, especially a thickened aqueous or aqueous alcoholic solution, a cream, foam, shampoo, powder, a gel, or an emulsion.

Customary the dyeing compositions are applied to the keratin-containing fiber in an amount of 50 to 100 g.

The dyeing compositions of the present invention are applied on the hair in a temperature range of 25 to 200, preferably 18 to 80, and most preferably from 20 to 40° C.

Preferred forms of formulations are ready-to-use compositions or multi-compartment dyeing devices or 'kits' or any of the multi-compartment packaging systems with compartments as described for example in U.S. Pat. No. 6,190,421, col 2, l. 16 to 31.

One preferred method of applying formulations comprising the dyes of formula (1) on the keratin-containing fiber, preferably the hair is by using a multi-compartment dyeing device or "kit" or any other multi-compartment packaging system, as described for example in WO 97/20545 on p. 4, l. 19 to l. 27.

The first compartment contains for example at least one dye of formula (1) and optionally further direct dyes and a basifying agent, and in the second compartment an oxidizing agent; or in the first compartment at least one dye of formula (1) and optionally futhter direct dyes, in the second compartment a basifying agent and in the third compartment an oxidizing agent.

The pH value of the ready-to-use dyeing compositions is usually from 2 to 11, preferably from 5 to 10.

Preferably the dyeing compositions, which are not stable to reduction, are prepared with oxidizing agent free compositions just before the dyeing process.

One preferred embodiment of the present invention relates to the formulation of dyes, wherein the dyes of formula (1) are in powder form.

Powder formulations are preferably used if stability and/or solubility problems as for example described in DE 197 13698, p. 2, l. 26 to 54 and p. 3, l. 51 to p. 4, l. 25, and p. 4, l. 41 to p. 5 l. 59, occur.

Suitable cosmetic hair-care formulations are hair-treatment preparations, e.g. hair-washing preparations in the form of shampoos and conditioners, hair-care preparations, e.g. pretreatment preparations or leave-on products such as sprays, creams, gels, lotions, mousses and oils, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidizing dyes, or natural hair colorants, such as henna or camomile.

For use on human hair, the dyeing compositions of the present invention can usually be incorporated into an aqueous cosmetic carrier. Suitable aqueous cosmetic carriers include, for example W/O, O/W, O/W/O, W/O/W or PIT emulsions and all kinds of microemulsions, creams, sprays, emulsions, gels, powders and also surfactant-containing foaming solutions, e.g. shampoos or other preparations, that are suitable for use on keratin-containing fibers. Such forms of use are described in detail in Research Disclosure 42448 (August 1999). If necessary, it is also possible to incorporate the dyeing compositions into anhydrous carriers, as described, for example, in U.S. Pat. No. 3,369,970, especially col 1, l. 70 to col 3, l. 55. The dyeing compositions according to the invention are also excellently suitable for the dyeing method described in DE-A-3 829 870 using a dyeing comb or a dyeing brush.

The constituents of the aqueous carrier are present in the dyeing compositions of the present invention in customary amounts, for example emulsifiers may be present in the dyeing compositions in concentrations from 0.5 to 30% b.w. and thickeners in concentrations from 0.1 to 25% b.w. of the total dyeing composition.

Further carriers for dying compositions are for example described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, especially on p. 243, l. 1 to p. 244, l. 12.

A shampoo has, for example, the following composition:

0.01 to 5% b.w. of the dye of formula (1);

8% b.w of disodium PEG5 laurylcitrate Sulfosuccinate, Sodium Laureth Sulfate;

20% b.w. of sodium cocoamphoacetate;

0.5% b.w. of methoxy PEG/PPG-7/3 aminopropyl dimethicone;

0.3% b.w. of hydroxypropyl guar hydroxypropytrimonium chloride;

2.5% b.w. of PEG-200 hydrogenated glyceryl pal mate; PEG-7 glyceryl cocoate;

0.5% b.w. of PEG-150 distearate;

2.2. % b.w of citric acid;

perfume, preservatives; and water ad 100%.

The dyes of formula (1) may be stored in a liquid to paste-like preparation (aqueous or nonaqueous) or in the form of a dry powder.

When the dyes and adjuvants are stored together in a liquid preparation, the preparation should be substantially anhydrous in order to reduce reaction of the compounds.

The dyeing compositions according to the invention may comprise any active ingredients, additives or adjuvants known for such preparations, like surfactants, solvents, bases, acids, perfumes, polymeric adjuvants, thickeners and light stabilisers.

The following adjauvents are preferably used in the hair dyeing compositions of the present invention:

non-ionic polymers, for example vinylpyrrolidone/vinyl acrylate copolymers, polyvinyl-pyrrolidone and vinylpyrrolidone/vinyl acetate copolymers and polysiloxanes;

cationic polymers, such as quaternised cellulose ethers, polysiloxanes having quaternary groups, dimethyldiallylammonium chloride polymers, copolymers of dimethyldiallylammonium chloride and acrylic acid, as available commercially under the name Merquat® 280 and the use thereof in hair dyeing as described, for example, in DE-A-4 421 031, especially p. 2, l. 20 to 49, or EP-A-953 334;

acrylamide/dimethyldiallylammonium chloride copolymers, diethyl-sulfate-quatemised dimethylaminoethyl methacrylate/vinylpyrrolidone copolymers, vinylpyrrolidone/-imidazolinium methochloride copolymers;

quaternised polyvinyl alcohol:

zwitterionic and amphoteric polymers, such as acrylamido-propyltrimethylammonium chloride/acrylate copolymers and octylacrylamide/methyl methacrylate/tert-butylaminoethyl methacrylate/2-hydroxypropyl methacrylate copolymers;

anionic polymers, such as, for example, polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert-butyl acrylamide terpolymers;

thickeners, such as agar, guar gum, alginates, xanthan gum, gum arabic, karaya gum, locust bean flour, linseed gums, dextrans, cellulose derivatives, e.g. methyl cellulose, hydroxyalkyl cellulose and carboxymethyl cellulose, starch fractions and derivatives, such amylose, amylopectin and dextrins, clays, e.g. bentonite or fully synthetic hydrocolloids such as, for example, polyvinyl alcohol;

structuring agents, such as glucose and maleic acid;

hair-conditioning compounds, such as phospholipids, for example soya lecithin, egg lecithin, cephalins, silicone oils, and conditioning compounds, such as those described in DE-A-19 729 080, especially p. 2, l. 20 to 49, EP-A-834 303, especially p. 2, l. 18-p. 3, l. 2, or EP-A-312 343, especially p. 2, l. 59-p. 3, l. 11;

protein hydrolysates, especially elastin, collagen, keratin, milk protein, soya protein and wheat protein hydrolysates, condensation products thereof with fatty acids and also quaternised protein hydrolysates;

perfume oils, dimethyl isosorbitol and cyclodextrins, solubilisers, such as ethanol, isopropanol, ethylene glycol, propylene glycol, glycerol and diethylene glycol, anti-dandruff active ingredients, such as piroctones, olamines and zinc Omadine, substances for adjusting the pH value;

panthenol, pantothenic acid, allantoin, pyrrolidonecarboxylic acids and salts thereof, plant extracts and vitamins;

cholesterol;

light stabilisers and UV absorbers as listed in Table below:

TABLE 1

UV absorbers which may be used in the dyeing compositions of the present invention

| No. | Chemical Name | CAS No. |
|---|---|---|
| 1 | (+/−)-1,7,7-trimethyl-3-[(4-methylphenyl)methylene]bicyclo-[2.2.1]heptan-2-one | 36861-47-9 |
| 2 | 1,7,7-trimethyl-3-(phenylmethylene)bicyclo[2.2.1]heptan-2-one | 15087-24-8 |
| 3 | (2-Hydroxy-4-methoxyphenyl)(4-methylphenyl)methanone | 1641-17-4 |

TABLE 1-continued

UV absorbers which may be used in the dyeing compositions of the present invention

| No. | Chemical Name | CAS No. |
|---|---|---|
| 4 | 2,4-dihydroxybenzophenone | 131-56-6 |
| 5 | 2,2',4,4'-tetrahydroxybenzophenone | 131-55-5 |
| 6 | 2-Hydroxy-4-methoxy benzophenone; | 131-57-7 |
| 7 | 2,2'-dihydroxy-4,4'-dimethoxybenzophenone | 131-54-4 |
| 8 | 2,2'-Dihydroxy-4-methoxybenzophenone | 131-53-3 |
| 9 | 1-[4-(1,1-dimethylethyl)phenyl]-3-(4-methoxyphenyl)propane-1,3-dione | 70356-09-1 |
| 10 | 3,3,5-Trimethyl cyclohexyl-2-hydroxy benzoate | 118-56-9 |
| 11 | Isopentyl p-methoxycinnamate | 71617-10-2 |
| 12 | Menthyl-o-aminobenzoate | 134-09-8 |
| 13 | Menthyl salicylate | 89-46-3 |
| 14 | 2-Ethylhexyl 2-cyano,3,3-diphenylacrylate | 6197-30-4 |
| 15 | 2-ethylhexyl 4-(dimethylamino)benzoate | 21245-02-3 |
| 16 | 2-ethylhexyl 4-methoxycinnamate | 5466-77-3 |
| 17 | 2-ethylhexyl salicylate | 118-60-5 |
| 18 | Benzoic acid, 4,4',4''-(1,3,5-triazine-2,4,6-triyltriimino)tris-,tris(2-ethylhexyl)ester; 2,4,6-Trianilino-(p-carbo-2'-ethylhexyl-1'-oxi)-1,3,5-triazine | 88122-99-0 |
| 19 | Benzoic acid, 4-amino-, ethyl ester, polymer with oxirane | 113010-52-9 |
| 20 | 2-Propenamide, N-[[4-[(4,7,7-trimethyl-3-oxobicyclo[2.2.1]hept-2-ylidene)methyl]phenyl]methyl]-, homopolymer | 147897-12-9 |
| 21 | Triethanolamine salicylate | 2174-16-5 |
| 22 | 2,2'-Methylene-bis-[6-(2H-benzotriazol-2-yl)-4-(1,1,3,3-tetramethyl-butyl)-phenol] | 103597-45-1 |
| 23 | 2,4-bis{[4-(2-ethylhexyloxy)-2-hydroxy-phenyl}-6-(4-methoxyphenyl)-(1,3,5)-triazine (Tinosorb S) | 187393-00-6 |
| 24 | Benzoic acid, 4,4'-[[6-[[4-[[(1,1-dimethylethyl)amino]carbonyl]-phenyl]amino]1,3,5-triazine-2,4-diyl]diimino]bis-, bis(2-ethylhexyl)-ester | 154702-15-5 |
| 25 | Phenol, 2-(2H-benzotriazol-2-yl)-4-methyl-6-[2-methyl-3-[1,3,3,3-tetramethyl-1-[(trimethylsilyl)oxy]disiloxanyl]propyl]- | 155633-54-8 |
| 26 | Dimethicodiethylbezalmalonate | 207574-74-1 |
| 27 | Benzoic acid, 2-[4-(diethylamino)-2-hydroxybenzoyl]-, hexyl ester | 302776-68-7 |
| 28 | 1,3,5-Triazine, 2,4,6-tris(4-methoxyphenyl)- | 7753-12-0 |
| 29 | 1,3,5-Triazine, 2,4,6-tris[4-[(2-ethylhexyl)oxy]phenyl]- | 208114-14-1 |
| 30 | 2-Propenoic acid, 3-(1H-imidazol-4-yl)- | 104-98-3 |
| 31 | Benzoic acid, 2-hydroxy-, [4-(1-methylethyl)phenyl]methyl ester | 94134-93-7 |
| 32 | 1,2,3-Propanetriol, 1-(4-aminobenzoate) | 136-44-7 |
| 33 | Benzeneacetic acid, 3,4-dimethoxy-a-oxo- | 4732-70-1 |
| 34 | 2-Propenoic acid, 2-cyano-3,3-diphenyl-, ethyl ester | 5232-99-5 |
| 35 | Anthralinic acid, p-menth-3-yl ester | 134-09-8 |
| 36 | 1,3,5-Triazine-2,4,6-triamine, N,N'-bis[4-[5-(1,1-dimethylpropyl)-2-benzoxazolyl]phenyl]-N''-(2-ethylhexyl)-or Uvasorb K2A | 288254-16-0 |
| 37 | 2-Hydroxy-4-methoxy benzophenone-5-sulfonic acid | 4065-45-6 |
| 38 | Alpha-(2-oxoborn-3-ylidene)toluene-4-sulphonic acid and its salts | 56039-58-8 |
| 39 | Methyl N,N,N-trimethyl-4-[(4,7,7-trimethyl-3-oxobicyclo[2,2,1]hept-2-ylidene)methyl]anilinium sulphate; | 52793-97-2 |
| 40 | 4-aminobenzoic acid | 150-13-0 |
| 41 | 2-phenyl-1H-benzimidazole-5-sulphonic acid | 27503-81-7 |
| 42 | 3,3'-(1,4-phenylenedimethylene)bis[7,7-dimethyl-2-oxo-bicyclo[2.2.1]heptane-1-methanesulfonic acid] | 90457-82-2 |
| 43 | 1H-Benzimidazole-4,6-disulfonic acid, 2,2'-(1,4-phenylene)bis-, disodium salt | 180898-37-7 |
| 44 | Benzenesulfonic acid, 3-(2H-benzotriazol-2-yl)-4-hydroxy-5-(1-methylpropyl)-, monosodium salt | 92484-48-5 |
| 45 | 1-Dodecanaminium, N-[3-[[4-(dimethylamino)benzoyl]amino]-propyl]N,N-dimethyl-, salt with 4-methylbenzenesulfonic acid (1:1) | 156679-41-3 |
| 46 | 1-Propanaminium, N,N,N-trimethyl-3-[(1-oxo-3-phenyl-2-propenyl)-amino]-, chloride | 177190-98-6 |
| 47 | 1H-Benzimidazole-4,6-disulfonic acid, 2,2'-(1,4-phenylene)bis- | 170864-82-1 |
| 48 | 1-Propanaminium, 3-[[3-[3-(2H-benzotriazol-2-yl)-5-(1,1-dimethyl-ethyl)-4-hydroxyphenyl]-1-oxopropyl]amino]-N,N-diethyl-N-methyl-, methyl sulfate (salt) | 340964-15-0 |
| 49 | 2,2'-bis(1,4-phenylene)-1H-benzimidazole-4,6-disulphonic acid mono sodium salt or Disodium phenyl dibenzimidazole tetrasulfonate or Neoheliopan AP | 349580-12-7, |

The use of UV absorbers can effectively protect natural and dyed hair from the damaging rays of the sun and increase the wash fastness of dyed hair.

Furthermore, the following UV absorbers or combinations may be used in the dyeing compositions according to the invention:

- cationic benzotriazole UV absorbers as for example described in WO 01/36396 especially on p. 1, l. 20 to p. 2, l. 24, and preferred on p. 3 to 5, and on p. 26 to 37;
- cationic benzotriazole UV in combination with antioxidants as described in WO 01/36396, especially on p. 11, l. 14 to p. 18;
- UV absorbers in combination with antioxidants as described in U.S. Pat. No. 5,922,310, especially in col 2, l. 1 to 3;
- UV absorbers in combination with antioxidants as described in U.S. Pat. No. 4,786,493, especially in col 1, 42 to col 2, l. 7, and preferred in col 3, 43 to col 5, l. 20;
- combination of UV absorbers as described in U.S. Pat. No. 5,830,441, especially in col 4, l. 53 to 56;
- combination of UV absorbers as described in WO 01/36396, especially on p. 11, l. 9 to 13; or
- triazine derivatives as described in WO 98/22447, especially on p. 1, l. 23 to p. 2, l. 4, and preferred on p. 2, l. 11 to p. 3, l. 15 and most preferred on p. 6 to 7, and 12 to 16.

Suitable cosmetic preparations may usually contain from 0.05 to 40% b.w., preferably from 0.1 to 20% b.w., based on the total weight of the composition, of one or more UV absorbers;
- consistency regulators, such as sugar esters, polyol esters or polyol alkyl ethers;
- fats and waxes, such as spermaceti, beeswax, montan wax, paraffins, fatty alcohols and fatty acid esters;
- fatty alkanolamides;
- polyethylene glycols and polypropylene glycols having a molecular weight of from 150 to 50 000, for example such as those described in EP-A-801 942, especially p. 3, l. 44 to 55,
- complexing agents, such as EDTA, NTA and phosphonic acids,
- swelling and penetration substances, such as polyols and polyol ethers, as listed extensively, for example, in EP-A-962 219, especially p. 27, l. 18 to 38, for example glycerol, propylene glycol, propylene glycol monoethyl ether, butyl glycol, benzyl alcohol, carbonates, hydrogen carbonates, guanidines, ureas and also primary, secondary and tertiary phosphates, imidazoles, tannins, pyrrole;
- opacifiers, such as latex;
- pearlising agents, such as ethylene glycol mono- and di-stearate;
- propellants, such as propane-butane mixtures, $N_2O$, dimethyl ether, $CO_2$ and air;
- antioxidants; preferably the phenolic antioxidants and hindered nitroxyl compounds disclosed in ip.com (IPCOM # 000033153D);
- sugar-containing polymers, as described in EP-A-970 687;
- quaternary ammonium salts, as described in WO 00/10517;
- Bacteria inhibiting agents, like preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% b.w., based on the solids content of the preparations;

The dyeing compositions according to the present invention generally comprise at least one surfactant.

Suitable surfactants are zwitterionic or ampholytic, or more preferably anionic, non-ionic and/or cationic surfactants.

Suitable anionic surfactants in the dyeing compositions according to the present invention include all anionic surface-active substances that are suitable for use on the human body. Such substances are characterised by an anionic group that imparts water solubility, for example a carboxylate, sulfate, sulfonate or phosphate group, and a lipophilic alkyl group having approximately 10 to 22 carbon atoms. In addition, glycol or polyglycol ether groups, ester, ether and amide groups and also hydroxy groups may be present in the molecule. The following are examples of suitable anionic surfactants, each in the form of sodium, potassium or ammonium salts or mono-, di- or tri-alkanolammonium salts having 2 or 3 carbon atoms in the alkanol group:

- linear fatty acids having 10 to 22 carbon atoms (soaps),
- ether carboxylic acids of formula $R-O-(CH_2-CH_2-O)_x-CH_2-COOH$, in which R is a linear alkyl group having 10 to 22 carbon atoms and x=0 or from 1 to 16,
- acyl sarcosides having 10 to 18 carbon atoms in the acyl group,
- acyl taurides having 10 to 18 carbon atoms in the acyl group,
- acyl isothionates having 10 to 18 carbon atoms in the acyl group,
- sulfosuccinic mono- and di-alkyl esters having 8 to 18 carbon atoms in the alkyl group and sulfosuccinic monoalkylpolyoxyethyl esters having 8 to 18 carbon atoms in the alkyl group and from 1 to 6 oxyethyl groups,
- linear alkane sulfonates having 12 to 18 carbon atoms,
- linear α-olefin sulfonates having 12 to 18 carbon atoms,
- α-sulfo fatty acid methyl esters of fatty acids having 12 to 18 carbon atoms,
- alkyl sulfates and alkyl polyglycol ether sulfates of formula $R'-O(CH_2-CH_2-O)_{x'}-SO_3H$, in which R' is a preferably linear alkyl group having 10 to 18 carbon atoms and x'=0 or from 1 to 12,
- mixtures of surface-active hydroxysulfonates according to DE-A-3 725 030;
- sulfated hydroxyalkylpolyethylene and/or hydroxyalkylenepropylene glycol ethers according to DE-A-3 723 354, especially p. 4, l. 42 to 62,
- sulfonates of unsaturated fatty acids having 12 to 24 carbon atoms and 1 to 6 double bonds according to DE-A-3 926 344, especially p. 2, l. 36 to 54,
- esters of tartaric acid and citric acid with alcohols which are addition products of approximately from 2 to 15 molecules of ethylene oxide and/or propylene oxide with fatty alcohols having from 8 to 22 carbon atoms, or
- anionic surfactants, as described in WO 00/10518, especially p. 45, l. 11 to p. 48, l. 3.

Preferred anionic surfactants are alkyl sulfates, alkyl polyglycol ether sulfates and ether carboxylic acids having 10 to 18 carbon atoms in the alkyl group and up to 12 glycol ether groups in the molecule, and also especially salts of saturated and especially unsaturated $C_8$-$C_{22}$carboxylic acids, such as oleic acid, stearic acid, isostearic acid and palmitic acid.

Surface-active compounds that carry at least one quaternary ammonium group and at least one $-COO^-$ or $-SO_3^-$ group in the molecule are terminated zwitterionic surfactants. Preference is given the so-called betaines, such as the N-alkylN,N-dimethylammonium glycinates, for example cocoalkyldimethylammonium glycinate, N-acylaminopropyl-N,N-dimethylammonium glycinates, for example cocoa-cylaminopropyldimethylammonium glycinate, and 2-alkyl-3-carboxymethyl-3-hydroxyethylimidazoline having from 8 to 18 carbon atoms in the alkyl or acyl group and also cocoa-cylaminoethylhydroxyethylcarboxymethyl glycinate. A preferred zwitterionic surfactant is the fatty acid amide derivative known by the CTFA name cocoamidopropyl betaine.

Ampholytic surfactants are surface-active compounds that, in addition to a $C_8$-$C_{18}$-alkyl or -acyl group and contain at least one free amino group and at least one —COOH or —$SO_3H$ group in the molecule and are capable of forming internal salts. Examples of suitable ampholytic surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having approximately from 8 to 18 carbon atoms in the alkyl group. Ampholytic surfactants to which special preference is given are N-cocoalkylaminopropionate, cocoacylaminoethylaminopropionate and $C_{12}$-$C_{18}$acylsarcosine.

Suitable non-ionic surfactants are described in WO 00/10519, especially p. 45, l. 11 to p. 50, l. 12. Non-ionic surfactants contain as hydrophilic group, for example, a polyol group, a polyalkylene glycol ether group or a combination of polyol and polyglycol ether groups. Such compounds are, for example:
- addition products of 2 to 30 mol of ethylene oxide and/or 0 to 5 mol of propylene oxide with linearar fatty alcohols having 8 to 22 carbon atoms, with fatty acids having 12 to 22 carbon atoms and with alkylphenols having 8 to 15 carbon atoms in the alkyl group,
- $C_{12}$-$C_{22}$ fatty acid mono- and di-esters of addition products of 1 to 30 mol of ethylene oxide with glycerol,
- $C_8$-$C_{22}$alkyl-mono- and -oligo-glycosides and ethoxylated analogues thereof,
- addition products of 5 to 60 mol of ethylene oxide with castor oil and hydrogenated castor oil,
- addition products of ethylene oxide with sorbitan fatty acid esters,
- addition products of ethylene oxide with fatty acid alkanolamides.

The surfactants which are addition products of ethylene and/or propylene oxide with fatty alcohols or derivatives of such addition products may either be products having a "normal" homologue distribution or products having a restricted homologue distribution. "Normal" homologue distribution are mixtures of homologues obtained in the reaction of fatty alcohol and alkylene oxide using alkali metals, alkali metal hydroxides or alkali metal alcoholates as catalysts. Restricted homologue distributions, on the other hand, are obtained when, for example, hydrotalcites, alkali metal salts of ether carboxylic acids, alkali metal oxides, hydroxides or alcoholates are used as catalysts.

The use of products having restricted homologue distribution may be preferred.

Examples of cationic surfactants that can be used in the dyeing compositions according to the invention are especially quaternary ammonium compounds. Preference is given to ammonium halides, such as alkyltrimethylammonium chlorides, dialkyldimethylammonium chlorides and trialkylmethylammonium chlorides, for example cetyltrimethylammonium chloride, stearyltrimethylammonium chloride, distearyidimethyl-lammonium chloride, lauryldimethylammonium chloride, lauryldimethylbenzylammonium chloride and tricetylmethylammonium chloride. Further cationic surfactants that can be used in accordance with the invention are quaternised protein hydrolysates.

Also suitable are cationic silicone oils, such as, for example, the commercially available products Q2-7224 (manufacturer Dow Corning; a stabilised trimethylsilylamodimethicone), Dow Corning 929 emulsion (comprising a hydroxylamino-modified silicone, which is also referred to as amodimethicone), SM-2059 (manufacturer: General Electric), SLM-55067 (manufacturer: Wacker) and also Abil®-Quat 3270 and 3272 (manufacturer: Th. Goldschmidt; diquaternary polydimethylsiloxanes, quaternium-80), or silicones, as described in WO 00/12057, especially p. 45, l. 9 to p. 55, l. 2.

Alkylamidoamines, especially fatty acid amidoamines, such as the stearylamidopropyl-dimethylamine obtainable under the name Tego Amid® 18 are also preferred as surfactants in the present dyeing compositions. They are distinguished not only by a good conditioning action but also especially by their good biodegradability.

Quaternary ester compounds, so-called "esterquats", such as the methyl hydroxyalkyl-dialkoyloxyalkylammonium methosulfates marketed under the trademark Stepantex®, are also very readily biodegradable.

An example of a quaternary sugar derivative that can be used as cationic surfactant is the commercial product Glucquate®, according to CTFA nomenclature a "lauryl methyl gluceth-10 hydroxypropyl dimonium chloride".

The alkyl-group-containing compounds used as surfactants may be single substances, but the use of natural raw materials of vegetable or animal origin is generally preferred in the preparation of such substances, with the result that the substance mixtures obtained have different alkyl chain lengths according to the particular starting material used.

A further preferred embodiment of the present invention relates to a method of treating keratin-containing fibers with styryl sulfide dyes of formula (1).

The method comprises treating the hair in the presence of a reducing agent.

Preferred reduction agents are for example thioglycolic acid or salts thereof, gycerine mono-thioglycolate, cysteine, homocysteine, 2-mercaptopropionic acid, 2-mercaptoethylamine, thiolactic acid and the salts thereof, thioglycerine, sodium sulfite, dithionithe, ammonium sulfite, sodium bisulfite, sodium metabisulfite, hydrochinon or phosphites.

In addition, the present invention relates to a method of
a. treating the keratin-containing fibers with a compound of formula (1),
b. wearing the coloured hair for the desired period of time,
c. removing the colour applied in step a. from hair by contacting the hair with an aqueous based colour removal composition containing a reduction agent capable of disrupting the —S—S— bonds between the dye molecule and the hair fiber surface to cause the dye molecule to become disassociated from the hair fiber.

Further, the present invention concerns a process, comprising treating the hair with a. a reduction agent, and b. at least one single styryl sulfide dye of formula (1) as defined above, and optionally c. with an oxidizing agent.

The sequence of the reaction steps is generally not important, the reduction agent can be applied first or in a final step.

Preferred is a process, which comprises treating the hair $a_1$) with at least one single dye of formula (1), and $b_1$) then with a reduction agent; or a process, which comprises treating the hair $a_2$) with a reduction agent and $b_2$) then with at least one single sulfide dye of formula (1) as defined above.

In the present invention preferred is further a process, which comprises treating the hair a) with a reduction agent, b) then with at least one dye of formula (1), and c) then with an oxidizing agent.

A further process of the present invention comprises contacting hair a) with at least one single dye of formula (1), b) then with a reduction agent, and c) then with an oxidizing agent.

Usually, the oxidizing agent is applied together with an acid or a base.

The acid is for example citric acid, phosphoric acid or tartrate acid.

The base is for example sodium hydroxide, ammonia or monoethanolamine.

The dyes of formula (1) are suitable for all-over dyeing of the hair, that is to say when dyeing the hair on a first occasion, and also for re-dyeing subsequently, or dyeing of locks or parts of the hair.

The dyes of formula (1) are applied on the hair for example by massage with the hand, a comb, a brush, or a bottle, or a bottle, which is combined with a comb or a nozzle.

In the processes for dyeing according to the invention, whether or not dyeing is to be carried out in the presence of a further dye will depend upon the color shade to be obtained.

Further preferred is a process for dyeing keratin-containing fibers which comprises treating the keratin-containing fiber with at least one dye of formula (1), a base and an oxidizing agent.

The oxidation dyeing process usually involves lightening, that is to say that it involves applying to the keratin-containing fibers, at basic pH, a mixture of bases and aqueous hydrogen peroxide solution, leaving the applied mixture to stand on the hair and then rinsing the hair. It allows, particularly in the case of hair dyeing, the melanin to be lightened and the hair to be dyed.

Lightening the melanin has the advantageous effect of creating a unified dyeing in the case of grey hair, and, in the case of naturally pigmented hair, of bringing out the color, that is to say of making it more visible.

In general, the oxidizing agent containing composition is left on the fiber for 0 to 15 minutes, in particular for 0 to 5 minutes at 15 to 45° C., usually in amounts of 30 to 200 g.

Oxidizing agents are for example persulfate or dilute hydrogen peroxide solutions, hydrogen peroxide emulsions or hydrogen peroxide gels, alkaline earth metal peroxides, organic peroxides, such as urea peroxides, melamine peroxides, or alkalimetalbromat fixations are also applicable if a shading powder on the basis of semi-permanent, direct hair dyes is used.

Further preferred oxidizing agents are oxidizing agents to achieve lightened coloration, as described in WO 97/20545, especially p. 9, l. 5 to 9, oxidizing agents in the form of permanent-wave fixing solution, as described in DE-A-19 713 698, especially p. 4, l. 52 to 55, and l. 60 and 61 or EP-A-1062940, especially p. 6, l. 41 to 47 (and in the equivalent WO 99/40895).

Most preferred oxidizing agent is hydrogen peroxide, preferably used in a concentration from about 2 to 30%, more preferably about 3 to 20% by, and most preferably from 6 to 12% b.w. the corresponding composition.

The oxidizing agents may be present in the dyeing compositions according to the invention preferably in an amount from 0.01% to 6%, especially from 0.01% to 1%, based on the total dyeing composition.

In general, the dyeing with an oxidative agent is carried out in the presence of a base, for example ammonia, alkali metal carbonates, earth metal (potassium or lithium) carbonates, alkanol amines, such as mono-, di- or triethanolamine, alkali metal (sodium) hydroxides, earth metal hydroxides or compounds of the formula

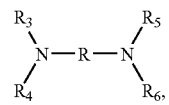

wherein is a propylene residue, which may be substituted with OH or $C_1$-$C_4$alkyl, $R_3$, $R_4$, $R_5$ and $R_6$ are independently or dependently from each other hydrogen, $C_1$-$C_4$alkyl or hydroxy-($C_1$-$C_4$)alkyl.

The pH-value of the oxidizing agent containing composition is usually about 2 to 7, and in particular about 2 to 5.

One preferred method of applying formulations comprising the dyes of formula (1) on the keratin-containing fiber, preferably the hair is by using a multi-compartment dyeing device or "kit" or any other multi-compartment packaging system, as described for example in WO 97/20545 on p. 4, l. 19 to l. 27.

The first compartment contains for example at least one dye of formula (1) and optionally further direct dyes and a basifying agent, and in the second compartment an oxidizing agent; or in the first compartment at least one dye of formula (1) and optionally further direct dyes, in the second compartment a basifiying agent and in the third compartment an oxidizing agent.

Generally the hair is rinsed after treatment with the dyeing solution and/or permanent-wave solution.

A further preferred embodiment of the present invention relates to a method of dyeing hair with oxidative dyes, which comprises a. mixing at least one dye of formula (1) and optionally at least one coupler compound and at least one developer compound, and an oxidizing agent, which optionally contains at least one further dye, and b. contacting the keratin-containing fibers with the mixture as prepared in step a.

The pH-value of the oxidizing agent free composition is usually from 3 to 11, and in particular from 5 to 10, and most particular about 9 to 10.

Preferably, a ready-to-use composition is prepared according to a first preferred embodiment by a process which comprises a preliminary step which involves separately storing, on the one hand, a composition (A) comprising, in a medium which is suitable for dyeing, at least one developer compound, especially selected from para-phenylenediamines and bis(phenyl)-alkylenediamines, and the acid-addition salts thereof, at least one coupler, especially selected from meta-phenylenediamines and the acid-addition salts thereof, and at least one dye of formula (1), on the other hand, a composition (B) containing, in a medium which is suitable for dyeing, at least one oxidizing agent and mixing (A) and (B) together immediately before applying this mixture to the keratin-containing fibers.

According to a second preferred embodiment for the preparation of the ready-to-use dye composition, the process includes a preliminary step which involves separately storing, on the one hand, a composition (A) comprising, in a medium which is suitable for dyeing, at least one developer compound, especially selected from para-phenylenediamines and bis(phenyl)alkylenediamines, and the acid-addition salts thereof, at least one coupler compound, especially selected from meta-phenylenediamines and the acid-addition salts thereof; on the other hand, a composition (A') comprising, in a medium which is suitable for dyeing, at least one dye of formula (1), and, finally, a composition (B) containing, in a medium which is suitable for dyeing, at least one oxidizing agent as defined above, and mixing them together at the time of use immediately before applying this mixture to the keratin-containing fibers.

The composition (A') used according to this second embodiment may optionally be in powder form, the dye(s) of formula (1) (themselves) constituting, in this case, all of the composition (A') or optionally being dispersed in an organic and/or inorganic pulverulent excipient.

When present in the composition A', the organic excipient may be of synthetic or natural origin and is selected in particular from crosslinked and non-crosslinked synthetic polymers, polysaccharides such as celluloses and modified or unmodified starches, as well as natural products such as sawdust and plant gums (guar gum, carob gum, xanthan gum, etc.).

When present in the composition (A'), the inorganic excipient may contain metal oxides such as titanium oxides, aluminium oxides, kaolin, talc, silicates, mica and silicas.

Ax very suitable excipient in the dyeing compositions according to the invention is sawdust.

The powdered composition (A') may also contain binders or coating products in an amount which preferably does not exceed approximately 3% b.w. relative to the total weight of composition (A'). These binders are preferably selected from oils and liquid fatty substances of inorganic, synthetic, animal or plant origin.

Furthermore, the present invention relates to a process of dyeing of keratin-containing fibers of the dyes of formula (1) with autooxidable compounds and optionally further dyes.

Furthermore, the present invention relates to a process for dyeing keratin-containing fibers with the dyes of formula (1) and capped diazotised compounds, which comprises, a. treating the keratin-containing fibers under alkaline conditions with at least one capped diazotised compound and a coupler compound, and optionally a developer compound and optionally an oxidizing agent, and optionally in the presence of a further dye, and optionally with at least one dye of formula (1); and b. adjusting the pH in the range of 6 to 2 by treatment with an acid, optionally in the presence of a further dye, and optionally at least one dye of formula (1), with the proviso that at least in one step a. or b. at least one dye of formula (1) is present.

The capped diazotised compound and coupler compound and optionally the oxidizing agent and developer compound can be applied in any desired order successively, or simultaneously.

Preferably, the capped diazotised compound and the coupler compound are applied simultaneously, in a single composition.

"Alkaline conditions" denotes a pH in the range from 8 to 10, preferably 9-10, especially 9.5-10, which are chieved by the addition of bases, for example sodium carbonate, ammonia or sodium hydroxide.

The bases may be added to the hair, to the dye precursors, the capped diazotised compound and/or the water-soluble coupling component, or to the dyeing compositions comprising the dye precursors.

Acids are for example tartaric acid or citric acid, a citric acid gel, a suitable buffer solution with optionally an acid dye.

The ratio of the amount of alkaline dyeing composition applied in the first stage to that of acid dyeing composition applied in the second stage is preferably about from 1:3 to 3:1, especially about 1:1.

Furthermore, the present invention relates to a process for dyeing keratin-containing fibers with the dyes of formula (1) and at least one acid dye.

The following Examples serve to illustrate the processes for dyeing without limiting the processes thereto. Unless specified otherwise, parts and percentages relate to weight. The amounts of dye specified are relative to the material being coloured.

T, s, d, q and J, wherein t is a triplett, s is singulett, d is duplett, q is a quartett, and J is a coupling constant, define the NMR spectra values.

EXAMPLES A

Preparation of New Compounds

EXAMPLE 1

Preparation of the Compound of Formula (101)

[Chemical structure of compound 101]

1. Alkylating Agent

A mixture of 15.4 g of 2,2-dithiodiethanol in 100 ml chloroform and 24.1 g pyridine are cooled with stirring to 0° C. and then 41.0 g of tosyl chloride are added in small amounts, maintaining the temperature at 0° C. by cooling externally.

After completion of the addition the mixture is left over night in the refrigerator to complete the reaction. The reaction mixture is mixed with a water/hydrochloric acid and ice slurry, the phases are separated, washed with water and dried.

The solution of toluenesulfonate diester is used as starting compound in the $2^{nd}$ reaction step.

2 Alkylation

The alkylation agent obtained in the $1^{st}$ reaction step is delivered from the solvent, dissolved in two equivalent amounts (18.8 g) of 4-methyl-pyridine. The temperature is raised to 70° C. and maintained at 60° C. during the following 12 hours.

3. Condensation

To the reaction mixture of the foregoing step 50 ml of isopropanol are added. Then the equivalent amount (30.0 g) of dimethylamino-benzaldehyde and a catalytic amount (3.6 g) of piperidine are added and the reaction mixture is stirred for 24 hours at 70° C.

The reaction product is precipitated by cooling, then separated by filtration and dried in vacuum to obtain 45 g of a reddish orange solid product.

The product is recristalized twice from methanol.

The product is characterized by the following data:

The HPLC-MS gives a main component of a dication of the mass 568

1H-NMR data in deuterated chloroform (128 scans)/360 MHz:

| Compound (101) | | | | |
|---|---|---|---|---|
| 9.62 | s | | .03 | Benzal (trace) |
| 8.528 | d | 6.7 | 3.98 | Py |
| 7.92 | d | 6.7 | 4.02 | Py |
| 7.781 | d | 16.6 | 2.03 | vinyl |
| 7.715 | d | 7.0 | 4.070 | tosilate |
| 7.58 | d | 6.1 | 4.04 | Phe |
| 7.476 | d | 6.8 | 4.02 | tosilate |
| 7.210 | d | 6.5 | 4.025 | Phe |
| 7.04 | d | 16.9 | 2.02 | vinyl |
| 6.76 | d | 6.4 | 4.05 | Phe |
| 4.71 | t | 6 | 4.00 | ethylene |
| 3.36 | t | 6 | 4.05 | etylene |
| 3.057 | s | | 12.087 | Dimethyl(amine) |
| 2.326 | s | | 5.90 | Me-tosilate |

EXAMPLE 2

Preparation of the Compound of Formula

1. Alkylating Agent

A mixture of 15.4 g 2,2-dithiodiethanol in 100 ml chloroform and 24.1 g pyridine are cooled with stirring to 0° C. and then 22.0 g of mesyl chloride are added in small amounts, maintaining the temperature by external cooling.

After completion of the addition the mixture is left over night in the refrigerator to complete the reaction.

The reaction mixture is mixed with a water/hydrochloric acid and ice slurry, the phases are separated, washed with water and dried.

The solution of methanesulfonate diester is used as starting compound in the $2^{nd}$ reaction step.

2. Alkylation

Two equivalents (18.8 g) of 4-methyl-pyridine are dissolved in the foregoing alkylation agent together with a solvent. The temperature is raised to reflux and maintained at 70° C. during the following 12 hours.

3. Condensation

The equivalent amount (24.0 g) of amino-benzaldehyde and a catalytic amount (3.6 g) of piperidine are added to the reaction mixture obtained in the $2^{nd}$ reaction step and the reaction mixture is stirred for 24 hours at 70° C.

The reaction product is precipitated by cooling, then separated by filtration and dried in vacuum to obtain 42 g of an orange solid product.

The product is recristallized twice from methanol.

The product is characterized by the following data:

The HPLC-MS gave a main component of a dication of the mass 512

1H-NMR data in deuterated chloroform (128 scans)/360 MHz:

| Compound (102) | | | | |
|---|---|---|---|---|
| 8.56 | d | 6.7 | 3.98 | Py |
| 8.38 | d | 6.7 | 4.02 | Py |
| 7.78 | d | 16.6 | 2.03 | vinyl |
| 7.51 | d | 6.1 | 4.04 | Phe |
| 7.28 | d | 6.5 | 4.025 | Phe |
| 7.06 | d | 16.9 | 2.02 | vinyl |
| 4.88 | t | 6 | 4.00 | ethylene |
| 3.14 | t | 6 | 4.05 | ethylene |
| 2.706 | s | | 5.90 | Mesylate |

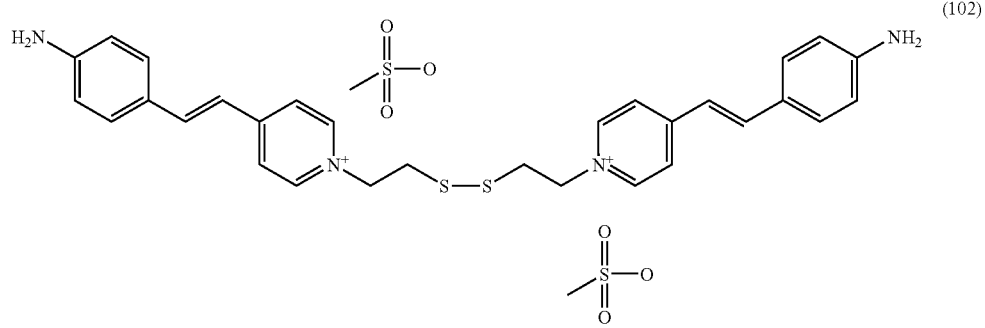

(102)

EXAMPLE 3

Preparation of the Compound of Formula

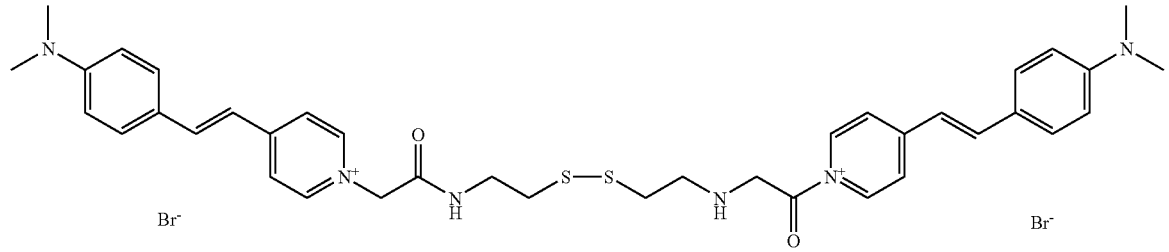

1. Alkylating Agent

A mixture of 25.4 g of cisteamine as dichlorohydrate in 100 ml water is cooled with stirring to 0° C. and 41.0 g of bromoacetic acid bromide are added in small amounts, maintaining the temperature at 0° C. by external cooling. The pH is adjusted with sodium hydroxide to 8.0.

After completion of the addition the mixture is left for one hour with agitation to complete the reaction.

The reaction mixture is separated by filtration, the solid washed with water and dried.

The alkylating agent used as starting compound in the $2^{nd}$ reaction step.

2. Alkylation

The alkylation agent obtained in the $1^{st}$ reaction step is added to 50 ml isopropaol and dissolved in two equivalent amounts (18.8 g) of 4-methyl-pyridine. The temperature is raised to 80° C. and maintained during the following 10 hours.

The product is recristallized twice from isopropanol.
The product is characterized by the following data:
The HPLC-MS gives a main component of a dication of the mass 682

1H-NMR data in deuterated chloroform (128 scans)/360 MHz:

| Compound (103) | | | | |
|---|---|---|---|---|
| 8.528 | d | 6.7 | 3.98 | Py |
| 7.92 | d | 6.7 | 4.02 | Py |
| 7.781 | d | 16.6 | 2.03 | vinyl |
| 7.58 | d | 6.1 | 4.04 | Phe |
| 7.210 | d | 6.5 | 4.025 | Phe |
| 7.04 | d | 16.9 | 2.02 | vinyl |
| 5.28 | s | | 4.04 | methylene |
| 3.65 | t | 6 | 4.00 | ethylene |
| 3.157 | s | | 12.087 | Dimethyl(amine) |
| 2.94 | t | 6 | 3.95 | ethylene |

EXAMPLE 4

Preparation of the Compound of Formula

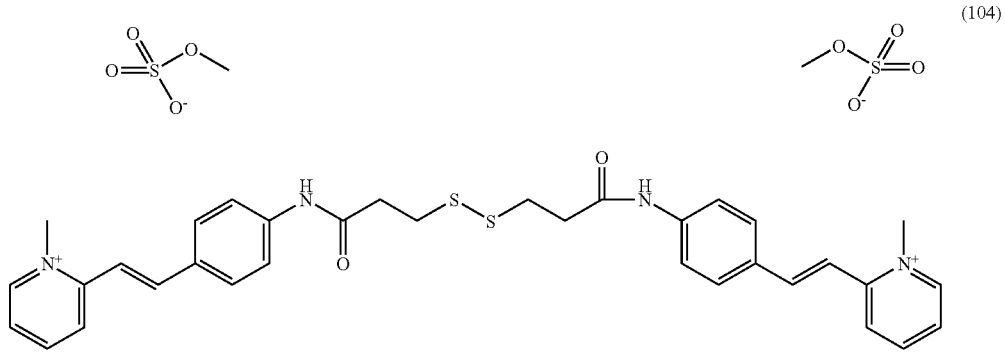

(104)

3. Condensation 20 ml of isopropanol are added to the reaction mixture obtained in the $2^{nd}$ reaction step. Then the equivalent amount (30.0 g) of dimethylamino benzaldehyde and a catylytic amount (3.6 g) of piperidine are added and the reaction mixture is stirred for 24 hours at 80° C.

The reaction product is precipitated by cooling, then separated by filtration and dried in vacuum to obtain 59 g of an orange solid product.

1. Acylating Agent

A mixture of 21.4 g 2,2-dithiodipropionic acid in 100 ml chloroform and 24.0 g thionyl chloride are added in small amounts, maintaining the temperature by external cooling.

After completion of the addition the mixture is heated to remove the formed gases and the reaction was finished. The solvent is removed by distillation under low pressure and the add chloride used as starting compound in the $2^{nd}$ reaction step.

2. Alkylation

The dimethylsulfate as alkylation agent is used without solvent and mixed with two equivalent amounts (18.8 g) 2-methyl-pyridine. The temperature is raised to 80° C. and maintained during the following 2 hours.

3. Condensation 50 ml of isopropanol are added to the reaction mixture of the foregoing step. The equivalent amount (24.0 g) of aminobenzaldehyde and a catalytic amount (3.6 g) of piperidine are added and the reaction mixture is stirred for 16 hours at 70° C.

The reaction product is precipitated by cooling, then separated by filtration and dried in vacuum to obtain 49 g of an orange solid product.

The product is recristallized twice from water.

4. Acylation

A mixture of 49 g of the fstyrene compound obtained in the $3^{rd}$ reaction step and 200 ml water are cooled with stirring to 0° C. and then 41.0 g of the acid chloride obtained in reaction step 1 dissolved in tetrahydrofurane are added in small amounts, maintaining the temperature by external cooling. The pH is adjusted to 6.0 by addition of sodium hydroxide.

After completion of the addition the mixture is left for one hour with agitation to complete the reaction. The reaction mixture is separated by filtration, the solid washed with water and dried.

The product may be used as such for dyeing applications.

The product is characterized by the following data:

1H-NMR data in deuterated chloroform (128 scans)/360 MHz:

| Compound (104) | | | | |
|---|---|---|---|---|
| 8.74 | d | 6.7 | 1.98 | Py |
| 8.41 | d | 6.7 | 4.02 | Py |
| 7.701 | m | | 12.070 | überlagert |
| 7.45 | d | 16.9 | 2.02 | vinyl |
| 4.390 | s | | 4.00 | methyl |
| 3.686 | s | | 5.89 | Methyl-sulfate |
| 3.09 | t | 6 | 4.05 | ethylene |
| 2.86 | t | 6 | 3.87 | ethylene |

EXAMPLE 5

Preparation of the Compound of Formula

1. Alkylating Agent

A mixture of 25.4 g of 2,2-dithiodiethylamine (cisteamine) as dichlorohydrate and 100 ml water is cooled with stirring to 0° C. and then 41.0 g of bromo acetic acid bromide are added in small amounts, maintaining the temperature by cooling externally. The pH is adjusted to 8.0 by addition of sodium hydroxide.

After completion of the addition the mixture is left for one hour with agitation to complete the reaction.

The reaction mixture is separated by filtration, the solid washed with water and dried.

The alkylating agent is used as starting compound in the $2^{nd}$ reaction step.

2 Alkylation

The alkylation agent obtained in the $1^{st}$ reaction step is delivered from the solvent and dissolved in two equivalents (18.8 g) 2-methyl-pyridine. The temperature is raised to 80° C. and maintained at 60° C. during the following 16 hours.

3. Condensation 50 ml of isopropanol are added to the reaction mixture obtained in the $2^{nd}$ reaction step. The equivalent amount (30.0 g) of dimethylamino benzaldehyde and a catalytic amount (3.6 g) of piperidine are added and the reaction mixture is stirred for 24 hours at 70° C.

The reaction product is precipitated by cooling, then separated by filtration and dried in vacuum to obtain 57 g of an orange solid product.

The product is recristallized twice from methanol.

The product is characterized by the following data:

The HPLC-MS gave a main component of a dication of the mass 682.

1H-NMR data in deuterated chloroform (128 scans)/360 MHz:

| Compound (105) | | | | |
|---|---|---|---|---|
| 8.6478 | d | 6.7 | 1.98 | Py |
| 8.360 | d | 6.7 | 2.02 | Py |
| 8.287 | t | 6.5 | 1.96 | Py |
| 7.838 | d | 16.6 | 2.03 | vinyl |
| 7.675 | d | 6.1 | 4.04 | Phe |
| 7.670 | t | 6.5 | 2.025 | Py |
| 7.210 | d | 16.9 | 2.02 | vinyl |
| 6.792 | d | 6.4 | 4.05 | Phe |
| 5.3 | s | | 4.01 | methylene |
| 4.71 | t | 6 | 4.00 | ethylene |
| 3.36 | t | 6 | 4.05 | etylene |
| 3.075 | s | | 12.087 | Dimethyl(amine) |

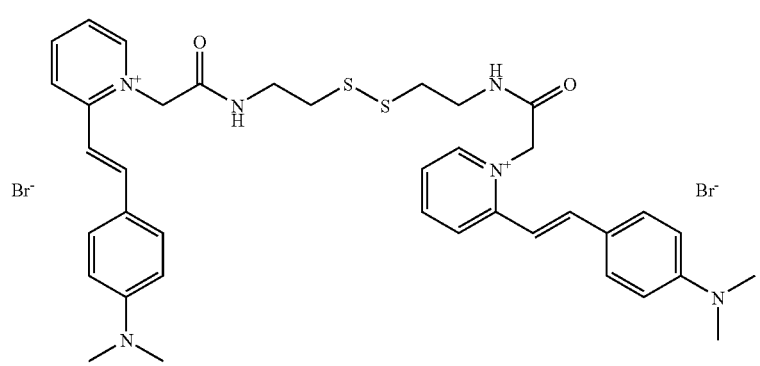

(105)

EXAMPLE 6

Preparation of the Compound of Formula

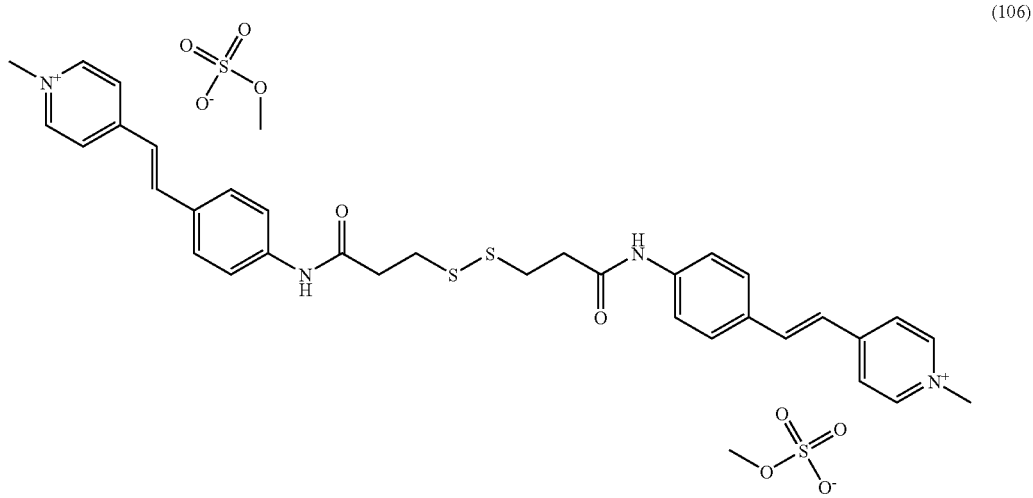

(106)

1. Acylating Agent 24.0 g of thionyl chloride are added to a mixture of 21.4 g of 2,2-dithiodipropionic acid in 100 ml chloroform in small amounts, maintaining the temperature by external cooling.

After completion of the addition the mixture is heated to remove the formed gases and the reaction is completed within one hour.

The solvent is removed by distillation under low pressure.

The acid chloride used as starting compound in the 2nd step

2. Alkylation

The dimethylsulfate as alkylation agent is used without solvent, with two equivalent amounts (18.8 g) of 4-methyl-pyridine. The temperature is raised to 80° C. and maintained at 80° C. during the following 2 hours.

3. Condensation 50 ml of isopropanole are added to the reaction mixture obtained in the $2^{nd}$ reaction step. Then the equivalent amount (24.0 g) of aminobenzaldehyde and a catalytic amount (3.6 g) of piperidine are added and the reaction mixture is stirred for 12 hours at 70° C.

The reaction product is precipitated by cooling, then separated by filtration and dried in vacuum to obtain 55 g of an orange solid product.

The product is recristallized twice from water.

4. Acylation

A mixture of 55 g of the styrene compound obtained in the $3^{rd}$ reaction step and 200 ml water is cooled with stirring to 0° C. and then 45.0 g of the acid chloride obtained in the $1^{st}$ reaction step, dissolved in tetrahydrofurane, are added in small amounts, maintaining the temperature at 0° C. by external cooling. The pH is adjusted to 7.0 by addition of sodium hydroxide.

After completion of the addition the mixture is left for one hour with agitation to complete the reaction.

The reaction mixture is separated by filtration; the solid washed with water and dried, The product may be used as such for dyeing applications.

The product is characterized by the following data:

1H-NMR data in deuterated chloroform (128 scans)/360 MHz:

| Compound (106) | | | | |
|---|---|---|---|---|
| 8.66 | d | 6.7 | 3.98 | Py |
| 8.10 | d | 6.7 | 4.02 | Py |
| 7.95 | d | 16.6 | 2.03 | vinyl |
| 7.68 | m | | 8.04 | overlaid |
| 7.210 | d | 6.5 | 4.025 | Phe |
| 7.28 | d | 16.9 | 2.02 | vinyl |
| 4.298 | s | | 6.00 | methyl |
| 3.69 | s | | 5.75 | Methyl-sulfate |
| 3.09 | t | 6 | 4.087 | ethylene |
| 2.85 | t | 6 | 3.90 | ethylene |

EXAMPLE 7

Preparation of the Compound of Formula

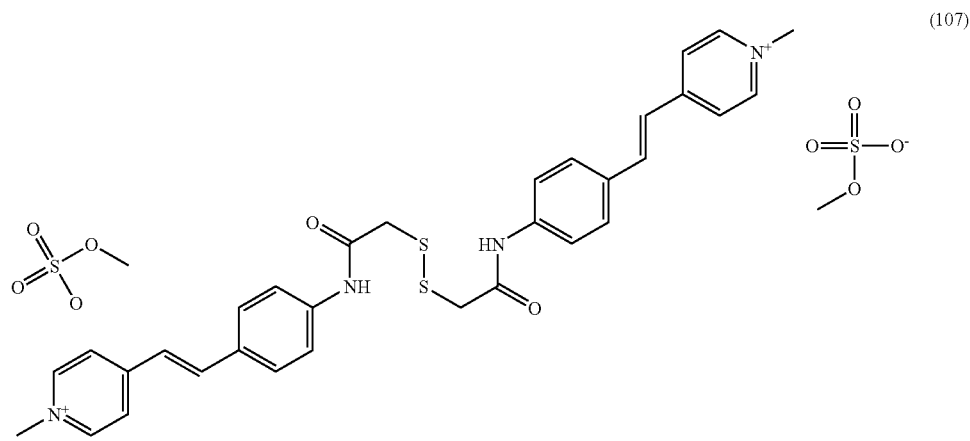

(107)

1. Acylating Agent

A mixture of 18.4 g 2,2-dithioglycolic acid in 100 ml chloroform and then 24.0 g of thionyl chloride are added in small amounts, maintaining the temperature by external cooling.

After completion of the addition the mixture is heated to remove the formed gases and the reaction is completed within one hour.

The solvent is removed by distillation under low pressure and the acid chloride is used as such in the $4^{th}$ reaction step.

2. Alkylation

The dimethylsulfate as alkylation agent is used without solvent with two equivalents (18.8 g) 4-methyl-pyridine. The temperature is raised to 70° C. and maintained at 80° C. during the following 2 hours.

3. Condensation 50 ml of isopropanol are added to the reaction mixture obtained in the $2^{nd}$ reaction step. The equivalent amount (24.0 g) of aminobenzaldehyde and a catalytic amount (3.6 g) of piperidine are added and the reaction mixture is stirred for 24 hours at 70° C.

The reaction product is precipitated by cooling, then separated by filtration and dried in vacuum to obtain 49 g of an orange solid product.

The product is recristallized twice from water. reaction step, diluted with 30 ml tetrahydrofurane are added in small amounts, maintaining the temperature at 0° C. by external cooling. The pH is adjusted to 6.0 by addition of sodium hydroxide.

4. Acylation

A mixture of 49 g of the styrene compound obtained in the $3^{rd}$ reaction step in 200 ml water are cooled with stirring to 0° C. and then 35.0 g of the acid chloride obtained in the $1^{st}$ After completion of the addition the mixture is left for one hour with agitation to complete the reaction. The reaction mixture is separated by filtration, the solid washed with water and dried.

The product may be used as such for dyeing applications.

The product is characterized by the following data:

1H-NMR data in deuterated chloroform (128 scans)/360 MHz

| Compound (107) | | | | |
|---|---|---|---|---|
| 9.62 | s | | .03 | ba |
| 8.528 | d | 6.7 | 3.98 | Py |
| 7.92 | d | 6.7 | 4.02 | Py |
| 7.781 | d | 16.6 | 2.03 | vinyl |
| 7.701 | d | 7.0 | 4.070 | tosilate |
| 7.58 | d | 6.1 | 4.04 | Phe |
| 7.210 | d | 6.5 | 4.025 | Phe |
| 7.04 | d | 16.9 | 2.02 | vinyl |
| 6.76 | d | 6.4 | 4.05 | Phe |
| 4.91 | t | 6 | 4.00 | methylene |
| 3.057 | s | | 12.087 | Dimethyl(amine) |

EXAMPLE 8

Preparation of the Compound of Formula

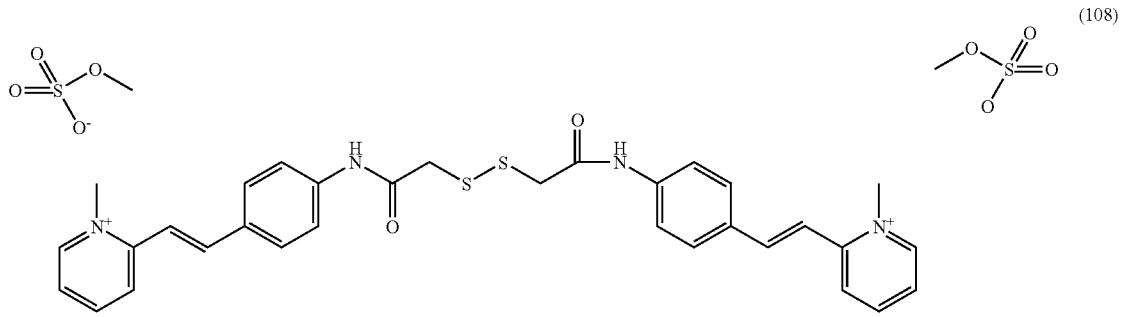

(108)

1. Acylating Agent

A mixture of 18.4 g 2,2-dithioglycolic acid in 100 ml chloroform and 24.0 g thionyl chloride are added in small amounts, maintaining the temperature at 20° C. by external cooling. After completion of the addition the mixture is heated to remove the formed gases and to complete the reaction.

The solvent is removed by distillation under low pressure and the acid chloride is used as such in the following step

2. Alkylation

The dimethylsulfate as alkylation agent is used without solvent, dissolved in two equivalent amounts (18.8 g) of 2-methylpyridine. The temperature is raised to 70° C. and maintained at 80° C. during the following 2 hours.

3. Condensation 50 ml of isopropanole are added to the reaction mixture obtained in the $2^{nd}$ reaction step. The equivalent amount (24.0 g) amino-benzaldehyde and a catalytic amount (3.6 g) of piperidine are added and the reaction mixture is stirred for 24 hours at 70° C.

The reaction product is precipitated by cooling, then separated by filtration and dried in vacuum to obtain 49 g of an orange solid product.

The product is recristallized twice from isopropanol.

4. Acylation

A mixture of 49 g of thestyrene compound obtained in the $3^{rd}$ reaction step and 200 ml water are cooled with stirring to 0° C. and then 41.0 g of acid chloride obtained in the 1st reaction step are added in small amounts, maintaining the temperature at by 0° C. external cooling.

The pH is adjusted to 6.0 by sodium hydroxide addition

After completion of the addition the mixture is left for one hour with agitation to complete the reaction.

The reaction mixture is separated by filtration, the solid washed with water and dried.

The product may be used for dyeing applications.

The product is characterized by the following data:

1H-NMR data in deuterated chloroform (128 scans)/360 MHz:

| Compound (108) | | | | |
|---|---|---|---|---|
| 8.6478 | d | 6.7 | 1.98 | Py |
| 8.360 | d | 6.7 | 2.02 | Py |
| 8.287 | t | 6.5 | 1.96 | Py |
| 7.838 | d | 16.6 | 2.03 | vinyl |
| 7.675 | d | 6.1 | 4.04 | Phe |
| 7.670 | t | 6.5 | 2.025 | Py |
| 7.210 | d | 16.9 | 2.02 | vinyl |
| 6.792 | d | 6.4 | 4.05 | Phe |
| 5.3 | s | | 4.01 | methylene |
| 3.075 | s | | 12.087 | Dimethyl(amine) |

EXAMPLE 9

Preparation of the Compound of Formula

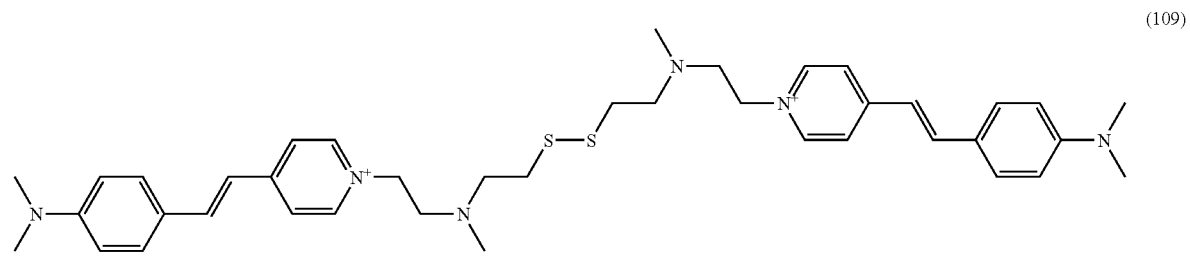

(109)

1. Alkylating Agent

A mixture of 21.5 g 2-hydroxyethyl-methylamine are neutralized with hydrochloric acid and evaporated to dryness. The salt is suspended in chloroform and cooled under stirring to 0° C. and then 41.0 g of thionyl chloride are added in small amounts, maintaining the temperature at by 0° C. external cooling.

After completion of the addition the reaction is completed by heating to reflux and degassing the mixture.

The solution is evaporated to dryness, the 2-chloroethyl-methylamine is used as chlorohydrate in the $2^{nd}$ reaction step.

2. Alkylation

The alkylation agent obtained in the $1^{st}$ reaction step is dissolved in n-butanol and two equivalent amounts (16.8 g) 4-methyl-pyridine are added. The temperature is raised to 120° C. and maintained during the following 6 hours. Than the temperature is lowered to 70° C.

3. Condensation

The equivalent amount (30.0 g) of dimethylaminobenzaldehyde and a catalytic amount (3.6 g) of piperidine are added to the reaction mixture obtained in the $2^{nd}$ reaction step and the reaction mixture is stirred for 24 hours at 70° C.

The reaction product is precipitated by cooling, then separated by filtration and dried in vacuum to obtain 50 g of an orange solid product.

The structure of the compound of formula

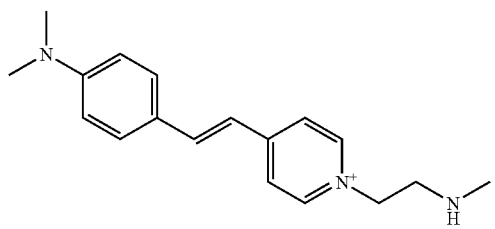

(109a)

is confirmed by 1H-NMR data in deuterated chloroform (128 scans)/360 MHz:

| Compound (109a) | | | |
|---|---|---|---|
| 8.585 | d | 6.7 | 1.98 | Py |
| 7.975 | d | 6.7 | 2.02 | Py |
| 7.846 | d | 16.6 | 1.03 | vinyl |
| 7.620 | d | 6.1 | 2.04 | Phe |
| 7.089 | d | 16.9 | 1.02 | vinyl |
| 6.798 | d | 6.4 | 2.05 | Phe |
| 4.574 | t | 6 | 2.00 | ethylene |
| 3.207 | t | 6 | 2.05 | etylene |
| 3.073 | s | | 6.087 | Dimethyl(amine) |
| 2.436 | s | | 3.00 | Methyl-amin |

4. Alkylating Agent

A mixture of 15.4 g of 2,2-dithiodiethanol in 100 ml chloroform and 24.1 g pyridine are cooled with stirring to 0° C.

and then 22.0 g of mesyl chloride are added in small amounts, maintaining the temperature at 0° C. by external cooling.

After completion of the addition the mixture is left over night in the refrigerator to complete the reaction.

The reaction mixture is mixed with a water/hydrochloric acid and ice slurry, the phases are separated, washed with water and dried.

The solution of methanesulfonate diester is used as such in the 5$^{th}$ reaction step.

5. Alkylation

Two equivalents (18.8 g) of the intermediate dye molecule obtained in the 3$^{rd}$ reaction step are dissolved in alkylation agent obtained in the 4$^{th}$ reaction step with a solvent. The temperature is raised to reflux and maintained at 70° C. during the following 12 hours.

The reaction mixture is cooled to ambient temperature with agitation and separated through filtration.

The solid is washed with chloroform and dryed.

The product is characterized by the following data:

1H-NMR data in deuterated chloroform (128 scans)/360 MHz

| Compound (109) | | | |
|---|---|---|---|
| 8.606 | d | 6.7 | 3.98 | Py |
| 7.920 | d | 6.7 | 4.02 | Py |
| 7.781 | d | 16.6 | 2.03 | vinyl |
| 7.696 | d | 7.0 | 4.070 | tosilate |
| 7.598 | d | 6.1 | 4.04 | Phe |
| 7.212 | d | 6.5 | 4.025 | Phe |
| 7.040 | d | 16.9 | 2.02 | vinyl |

| -continued Compound (109) | | | |
|---|---|---|---|
| 6.772 | d | 6.4 | 4.05 | Phe |
| 4.815 | t | 6 | 4.00 | ethylene |
| 3.792 | t | 6 | 3.8 | ethylene |
| 3.659 | t | 6 | 4.05 | etylene |
| 3.059 | s | | 12.087 | Dimethyl(amine) |
| 2.928 | t | 6 | 3.9 | ethylene |
| 2.783 | s | | 5.4 | Methyl-amin |
| 2.326 | s | | 5.90 | Me-tosilate |

EXAMPLE 10

Preparation of the Compound of Formula

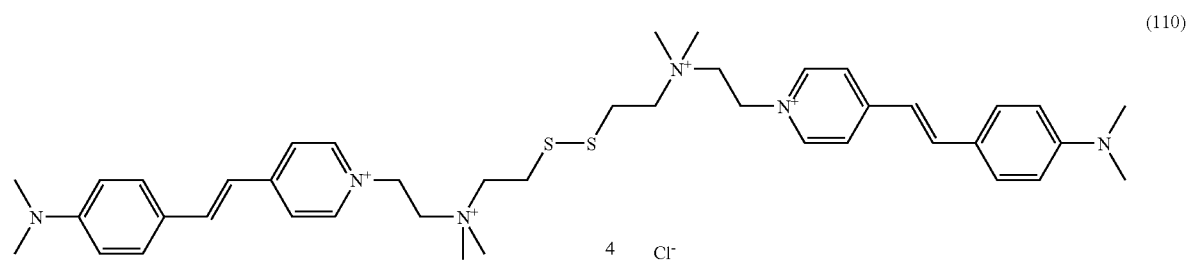

(110)

1. Alkylation

The alkylation agent 2-chloroethyl-N,N-dimethylamine is dissolved in n-butanol and equivalent amounts (18.028 g) of 4-methyl-pyridine are added. The temperature is raised to 120° C. and maintained at 120° C. during the following 6 hours. Than the temperature is lowered to 70° C., 2. Condensation The equivalent amount (30.0 g) of dimethylamino-benzaldehyde and a catalytic amount (3.6 g) of piperidine are added to the reaction mixture obtained in the 1$^{st}$ reaction step and the reaction mixture is stiffed for 24 hours at 70° C.

The reaction product is precipitated by cooling, then separated by filtration and dried in vacuum to obtain 50 g of an orange solid product.

The structure corresponding to formula

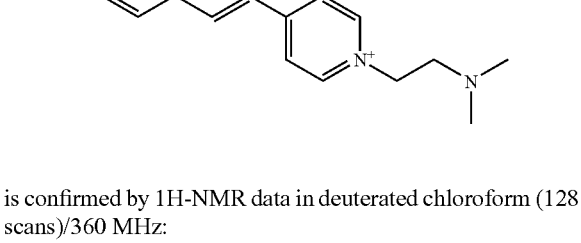

(110a)

is confirmed by 1H-NMR data in deuterated chloroform (128 scans)/360 MHz:

| Compound (110a) | | | |
|---|---|---|---|
| 8.623 | d | 6.7 | 1.98 | Py |
| 7.992 | d | 6.7 | 2.02 | Py |
| 7.819 | d | 16.6 | 1.03 | vinyl |
| 7.528 | d | 6.1 | 2.06 | Phe |
| 7.082 | d | 16.9 | 1.02 | vinyl |
| 6.742 | d | 6.4 | 2.05 | Phe |
| 4.774 | t | 6 | 2.00 | ethylene |
| 3.157 | t | 6 | 2.05 | etylene |
| 3.073 | s | | 6.087 | Dimethyl(amine) |
| 2.590 | | | 6.09 | Dimethyl-am |

3. Alkylating Agent

A mixture of 15.4 g of 2,2-dithiodiethanol in 100 ml chloroform and 24.1 g pyridine are cooled with stirring to 0° G and then 41.09 of tosyl chloride are added in small amounts, maintaining the temperature at 0° C. by cooling externally.

After completion of the addition the mixture is left over night in the refrigerator to complete the reaction.

The reaction mixture is mixed with a water/chlorhidric acid and ice slurry, the phases are separated, washed with water and dried.

The solution of toluenesutfonate diester is used as starting compound in the 4$^{th}$ reaction step.

4. Alkylation

Two equivalents (56 g) of the intermediate dye molecule are dissolved in the foregoing alkylation agent obtained in the 4$^{th}$ reaction step with solvent. The temperature is raised to reflux and maintained at 70° C. during the following 12 hours.

The reaction mixture is cooled to ambient temperature with agitation and separated through filtration.

The solid is washed with chloroform and dryed.

The product is characterized by the following data:

1H-NMR data in deuterated chloroform (128 scans)/360 MHz:

| Compound (110) | | | | |
|---|---|---|---|---|
| 9.62 | s | | .03 | ba |
| 8.628 | d | 6.7 | 4.00 | Py |
| 7.969 | d | 6.7 | 4.04 | Py |
| 7.781 | d | 16.6 | 2.03 | vinyl |
| 7.701 | d | 7.0 | 4.070 | tosilate |
| 7.58 | d | 6.1 | 4.04 | Phe |
| 7.239 | d | 6.5 | 4.025 | Phe |
| 7.067 | d | 16.9 | 2.02 | vinyl |
| 6.813 | d | 6.4 | 4.05 | Phe |
| 4.867 | t | 6 | 4.00 | ethylene |
| 3.718 | t | 6 | 4.05 | ethylene |
| 3.36 | t | 6 | 3.89 | ethylene |
| 3.057 | s | | 12.087 | Dimethyl(amine) |
| 2.959 | s | | 12.12 | dimethyl |
| 2.346 | s | | 6.070 | Me-tosilate |

EXAMPLE B

Application Examples

The washing fastness of the dyed hair is analyzed by the Grey scale according to Industrial organic pigments by Herbst&Hunger, 2nd ed. engl. S. 61) Nr 10: DIN 54 0018-1982, "Herstellung und Bewertung der Aenderung der Farbe", ISO 105-A02-1993.

In the following application examples compositions within the below given definitions are used:

Solution 1 (Permanent Lotion, pH 8.2):

Aqua, Ammonium Thioglycolate, Ammonium Bicarbonate, Ethoxydiglycol, Hexylene Glycol, Thioglycolic Acid; Thiolactic Acid, PEG-60 Hydrogenated Castor Oil, Glycine, Etidronic Acid, Isoceteth-20, Polysilicone-9, Styrene/PVP Copolymer, Trideceth-12, Amodimethicone, Cetrimonium Chloride, Ammonium Hydroxide, Polyquaternium-6, Isopropyl Alcohol, Alcohol denat., Simethicone, Parfum Solution 2 (Permanent Fixation, pH 3.9):

Based on:

Aqua, Hydrogen Peroxide, Propylene Glycol, Lauryldimonium Hydroxypropyl Hydrolyzed Wheat Protein, PEG-5 Cocamide, Sodium Cocoamphoacetate, Polyquaternium-35, Coco-Betaine, Acetaminophen, Phosphoric Acid, Sodium Chloride, Parfum Solution 3 (Dyeing Solution):

0.1% of the dye is dissolved in a 10% solution of a non-ionic surfactant (Plantacare 200UP, Henkel) adjusted to pH 9.5 using citric acid or monoethanolamine.

APPLICATION EXAMPLE B1

50 mg of compound of formula (ELV 1703) according to example AX, is dissolved in 10 g methanol and then 40 g of plantaren solution (10% in water with pH=9.5) is added: This red dyeing solution is applied on the dry hair (two blond, two middle blond, two brown and two damaged hair strands) at room temperature and allowed to stand for 20 min. at room temperature. Then, the strands are rinsed under tap water (Water temperature: 37° C.+/−1° C.; flow rate of water: 5-6 l/min.) and dried 12 hours at room temperature.

Washing fastness: 10× washed with shampoo.

Results:

| Results: | | |
|---|---|---|
| Strand | Colour result | Washing fastness |
| blond | Orange/good | 2-3 |
| middelblond | Orange/good | 3-4 |
| brown | Orange/good | 4-5 |
| damaged | Orange/good | 3 |

APPLICATION EXAMPLE B2

A 0.1% Ammoniumthioglycolate solution (pH adjusted with Ammonia and Citric acid to 8) is applied on shampooed hair (two blond, two middle blond, two brown and two damaged hair strands) at room temperature and allowed to stand for 10 min. Then, the strands are rinsed under tap water (Water temperature: 37° C.+/−1° C.; flow rate of water: 5-6 l/min.), and the towel dry strands are treated with the 0.1%, by weight colouring material solution of example BI allowed to stand for 20 min and then rinsed under tap water (Water temperature: 37° C.+/−1° C.; flow rate of water 5-6 l/min.). Then, the towel dry strands are treated with the solution 2 (permanent fixation) and allowed to stand for 10 min. Then the strands are rinsed under tap water (Water temperature: 37° C.+/−1° C.; flow rate of water: 5-6 l/min.) and dried 12 hours at room temperature.

Washing fastness: 10× washed with shampoo.

| Results: | | |
|---|---|---|
| Strand | Colour | Washing fastness |
| blond | Orange/good | 3-4 |
| middelblond | Orange/good | 3-4 |
| brown | Orange/good | 4-5 |
| damaged | Orange/good | 3 |

APPLICATION EXAMPLE B3

A solution 1 (permanent lotion) is applied on shampooed hair (two blond, two middle blond, two brown and two damaged hair strands) at room temperature and allowed to stand for 10 min. Then, the strands are rinsed under tap water (Water temperature: 37° C.+/−1° C.; flow rate of water: 5-6 l/min.), and the towel dry strands are treated with the 0.1%, by weight colouring material solution of example B1 allowed to stand for 20 min and then rinsed under tap water (Water temperature: 37° C.+/−1° C.; flow rate of water: 5-6 l/min.). Then, the towel dry strands are treated with the solution 2 (permanent fixation) at room temperature and allowed to stand for 10 min. Then the strands are rinsed under tap water (Water temperature: 37° C.+/−1° C.; flow rate of water: 5-6 l/min.) and dried 12 hours at room temperature.

Washing fastness: 10× washed with shampoo.

| Results: | | |
|---|---|---|
| Strand | Colour | Washing fastness |
| blond | Orange/very good | 5 |
| middelblond | Orange/very good | 5 |
| brown | Orange/very good | 5 |
| damaged | Orange/very good | 5 |

EXAMPLE B4

50 mg of compound of formula (104) is dissolved in 10 g methanol and then 40 g of water is added: This yellow dyeing solution is applied on the dry hair (two blond, two middle blond, and two damaged hair strands) at room temperature and allowed to stand for 20 min. at room temperature. Then, the strands are rinsed under tap water (Water temperature: 37° C.+/−1° C.; flow rate of water: 5-6 l/min.) and dried 12 hours.

Washing fastness: 10× washed with shampoo.

Results:

| Results: | | |
|---|---|---|
| Strand | Colour result | Washing fastness |
| blond | Yellow/good | 2 |
| middelblond | Yellow/middle | 4 |
| damaged | Yellow/good | 2-3 |

EXAMPLE B5

A solution 1 (permanent lotion) is applied on shampooed hair (two blond, two middle blond, and two damaged hair strands) at room temperature and allowed to stand for 10 min. Then, the strands are rinsed under tap water (Water temperature: 37° C.+/−1° C.; flow rate of water: 5-6 l/min.) and the towel dry strands are treated with the 0.1% by weight colouring material solution of example B4 at room temperature, allowed to stand for 20 min and then rinsed under tap water (Water temperature: 37° C.+/−1° C.; flow rate of water: 5-6 l/min.). Then, the towel dry strands are treated with the solution 2 (permanent fixation) at room temperature and allowed to stand for 10 min. Then the strands are rinsed under tap water (Water temperature: 37° C.+/−1° C.; flow rate of water: 56 l/min.) and dried 12 hours at room temperature.

Washing fastness: 10× washed with shampoo.

| Results: | | |
|---|---|---|
| Strand | Colour | Washing fastness |
| blond | Yellow/good | 4 |
| middelblond | Yellow/good | 4 |
| damaged | Yellow/good | 3 |

The invention claimed is:

1. A method of dyeing keratin-containing fibers comprising treating the fiber with at least one sulfide dye of formula (1)

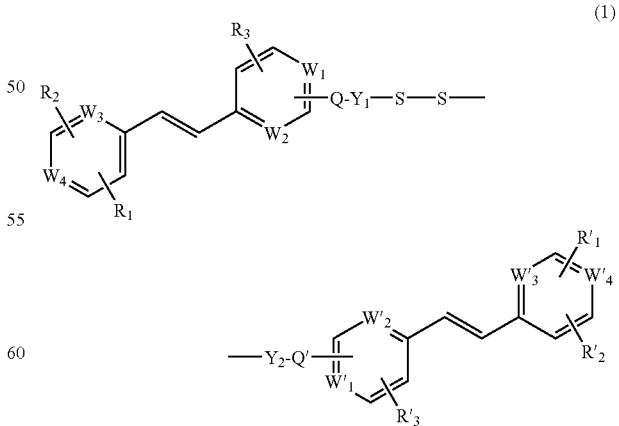

their salts, isomers, hydrates and other solvates, wherein
$R_1$, $R'_1$, $R_2$, $R'_2$, $R_3$ and $R'_3$, independently from each other are hydrogen; $C_1$-$C_{20}$alkyl or $C_1$-$C_{20}$alkoxy, which may be substituted by one or more $C_1$-$C_5$alkoxy, halogen, —$NH_2$, mono-$C_1$-$C_5$alkylamino, di-$C_1$-$C_5$alkylamino, —$NO_2$ or hydroxy; $C_3$-$C_6$cycloalkyl; —C(O)H; —C(O)—$C_1$-$C_5$alkyl; halogen; $NO_2$; OH; phenyl, which may be substituted by one or more $C_1$-$C_5$alkyl, $C_1$-$C_5$alkoxy, halogen, —$NH_2$, mono-$C_1$-$C_5$alkylamino, di-$C_1$-$C_5$alkylamino, —$NO_2$ or hydroxy; or a radical of formula —$NR_4R_5$, wherein $R_4$ and $R_5$ independently from each other are hydrogen; $C_1$-$C_{12}$alkyl, which may be substituted by one or more $C_1$-$C_5$alkyl, $C_1$-$C_5$-alkoxy, hydroxy or —(CO)—H; —(CO)—$C_1$-$C_5$alkyl; phenyl or phenyl-$C_1$-$C_4$alkyl, wherein the phenyl moiety may be substituted by one or more $C_1$-$C_5$alkyl, $C_1$-$C_5$alkoxy, halogen, —$NH_2$, mono-$C_1$-$C_5$alkylamino, di-$C_1$-$C_5$alkylamino, —$NO_2$, carboxy or hydroxy;

$W_1$, $W'_1$, $W_2$, $W'_2$, $W_3$, $W'_3$, $W_4$ or $W'_4$, independently from each other are —CH— or —$N^+$—; wherein only one of $W_1/W'_1$, $W_2/W'_2$, $W_3/W'_3$, $W_4/W'_4$' is —$N^+$; and the bivalent radical -Q-Z—Y—S—S—Y'—Z'-Q'- is bonded to $W_1$ or $W_2$ and $W'_1$ or $W'_2$ respectively;

$Y_1$ and $Y_2$ independently from each other are $C_1$-$C_{10}$alkylene; $C_5$-$C_{10}$cycloalkylene; $C_5$-$C_{12}$arylene; or $C_5$-$C_{12}$arylene-($C_1$-$C_{10}$alkylene);

Q and Q' independently from each other are a direct bond; —C(O)—; —C(O)O—; —OCO—; —N($R_6$)—;

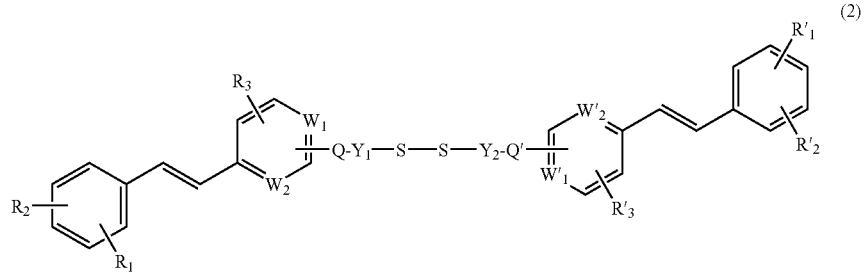

—C(O)N($R_6$)—; —($R_6$)NC(O)—; —O—; —S—; —S(O)—; or —S(O)$_2$—; and $R_6$ and $R_7$ independently from each other are hydrogen; $C_1$-$C_{14}$alkyl; $C_2$-$C_{14}$alkenyl; $C_6$-$C_{12}$aryl; $C_6$-$C_{12}$aryl-$C_1$-$C_{10}$alkyl; or $C_1$-$C_{10}$alkyl($C_5$-$C_{12}$aryl).

2. The method according to claim 1, wherein $Y_1$ and $Y_2$ are $C_1$-$C_{10}$alkylene; or $C_5$-$C_{10}$cycloalkylene.

3. The method according to claim 1, wherein $Y_1$ and $Y_2$ are $C_1$-$C_5$alkylene.

4. The method according to claim 1, wherein $R_1$, $R'_1$, $R_2$, $R'_2$, $R_3$ and $R'_3$, independently from each other are hydrogen; $C_1$-$C_5$alkyl; $NO_2$; or a radical of formula (1a) —$NR_4R_5$, wherein $R_4$ and $R_5$ independently from each other are hydrogen; or $C_1$-$C_5$alkyl.

5. The method according to claim 4, wherein $R_1$, $R'_1$, $R_2$, $R'_2$, $R_3$ and $R'_3$, independently from each other are hydrogen; $C_1$-$C_5$alkyl; $NO_2$; or $NH_2$.

6. The method according to claim 1, wherein $R_1$, $R'_1$, $R_2$, $R'_2$, $R_3$ and $R'_3$ are hydrogen.

7. The method according to claim 1, wherein $Q_1$ and Q' are a direct bond or —($R_6$)NC(O)—, wherein $R_6$ is hydrogen; or $C_1$-$C_5$alkyl.

8. The method according to claim 1, wherein sulfide dyes of formula (1) are of formula (2)

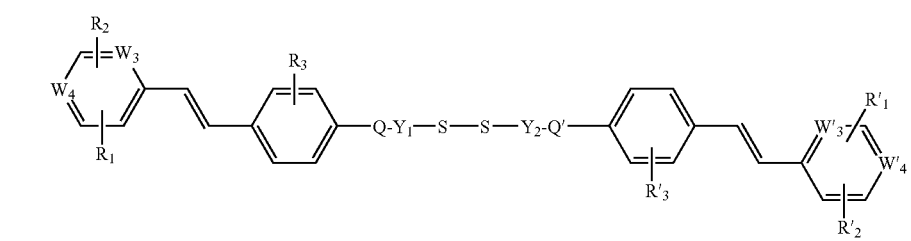

wherein
one of $W_1/W'_1$ or $W_2/W'_2$, is —$N^+$—, the other is —CH—; and
the biradical -Q-Y—S—S—Y'-Q' is bonded to —$N^+$; and $R_1$, $R'_1$, $R_2$, $R'_2$, $R_3$, $R'_3$, $W_1$, $W'_1$, $W_2$, $W'_2$, Q, Q', $Y_1$ and $Y_2$ are defined as in claim 1.

9. The method according to claim 1, wherein sulfide dyes of formula (1) are of formula (3)

(3)

wherein
one of $W_3/W'_3$ or $W_4/W'_4$ is —$N^+$—, the other is —CH—; and $R_1$, $R'_1$, $R_2$, $R'_2$, $R_3$, $R'_3$, $W_3$, $W'_3$, $W_4$, $W'_4$, Q, Q', $Y_1$ and $Y_2$ are defined as in claim 1.

10. The method according to claim 8, wherein sulfide dyes of formula (2) are of formula (2a) or (2b)

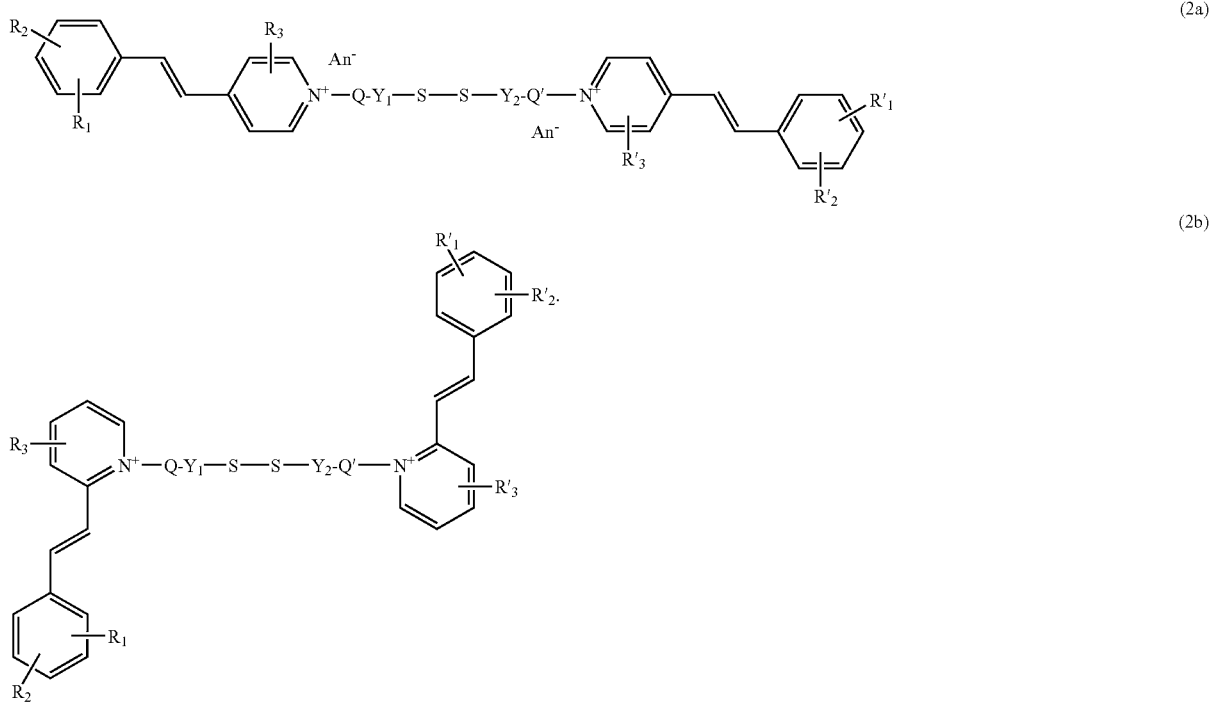

(2a)

(2b)

wherein An⁻ is anion and $R_1$, $R'_1$, $R_2$, $R'_2$, $R_3$, $R'_3$, Q, Q', $Y_1$ and $Y_2$ are defined as in claim 1.

11. The method according to claim 1, wherein
$R_1$ is identical to $R_1'$;
$R_2$ is identical to $R_2'$;
$R_3$ is identical to $R_3'$;
Q is identical to Q'; and
$Y_1$ is identical to $Y_2$.

12. The method according to claim 1 wherein the dyeing is carried out in presence of a reducing agent.

13. The method according to claim 12, wherein the reducing agent is selected from thioglycol acid or salts thereof, gycerine monothioglycolate, cystein, 2-mercaptopropionic acid, 2-mercaptoethylamine, thiolactic acid, thioglycerine, sodium sulfite, dithionithe, ammonium sulfite, sodium bisulfite, sodium metabisulfite and hydrochinon.

14. The method according to claim 1, comprising treating the keratin-containing fiber
a) optionally with a reduction agent, and
b) at least one single styryl sulfide dye of formula (1) and
c) optionally with an oxydizing agent.

15. The method according to claim 1, comprising
a) dyeing the keratin-contining fiber with a sulfide dyes of formula (1),
b) wearing the coloured hair for the desired period of time and
c) removing the colour applied in step a) from hair by contacting the hair with an aqueous based colour removal composition containing a reducing agent.

16. A hair dyeing composition comprising
(a) 0.001 to 5 of at least one dye of formula (1) as defined in claims 1;
(b) 1 to 40% b.w. of a solvent; and
(c) 0.01 to 20% b.w. of an adjuvant.

17. The composition according to claim 16 in form of a shampoo, conditioner, gel or emulsion.

18. The composition according to claim 16 comprising at least one single dye of formula (1), and a direct dye and/or a reactive dye.

19. The method according to claim 9, wherein sulfide dyes of formula (3) are of formula (3a) or (3b)

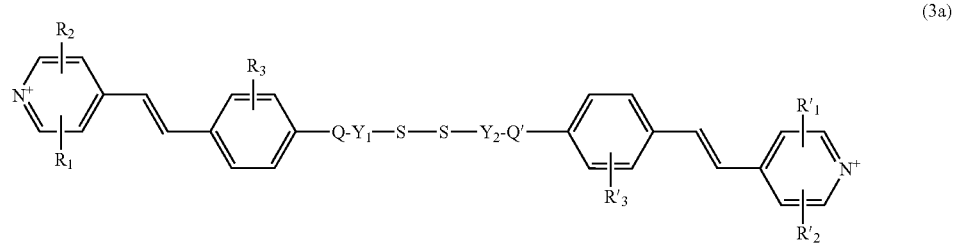

(3a)

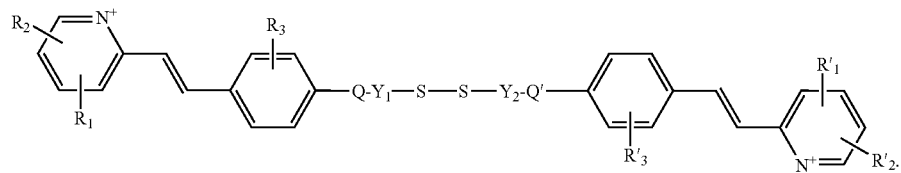
(3b)
wherein $R_1$, $R'_1$, $R_2$, $R'_2$, $R_3$, $R'_3$, Q, Q', $Y_1$ and $Y_2$ are defined as in claim 1.
* * * * *